(12) United States Patent
Deng et al.

(10) Patent No.: US 12,740,989 B2
(45) Date of Patent: Sep. 22, 2026

(54) NOTCH SIGNALING INHIBITORS FOR TREATING OBESITY AND METABOLIC DISORDERS

(71) Applicant: Purdue Research Foundation, West Lafayette, IN (US)

(72) Inventors: Meng Deng, West Lafayette, IN (US); Di Huang, Malden, MA (US); Shihuan Kuang, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 708 days.

(21) Appl. No.: 18/017,384

(22) PCT Filed: Jul. 23, 2021

(86) PCT No.: PCT/US2021/042867
§ 371 (c)(1),
(2) Date: Jan. 20, 2023

(87) PCT Pub. No.: WO2022/020658
PCT Pub. Date: Jan. 27, 2022

(65) Prior Publication Data

US 2023/0277549 A1 Sep. 7, 2023

Related U.S. Application Data

(60) Provisional application No. 63/055,410, filed on Jul. 23, 2020.

(51) Int. Cl.
*A61K 31/55* (2006.01)
*A61K 9/19* (2006.01)
(Continued)

(52) U.S. Cl.
CPC ................ *A61K 31/55* (2013.01); *A61K 9/19* (2013.01); *A61K 31/19* (2013.01); *A61K 31/192* (2013.01);
(Continued)

(58) Field of Classification Search
CPC .... A61K 31/19; A61K 31/192; A61K 31/335; A61K 31/4164; A61K 31/417;
(Continued)

(56) References Cited

U.S. PATENT DOCUMENTS

| | | | |
|---|---|---|---|
| 2005/0054633 | A1 | 3/2005 | Flohr et al. |
| 2013/0281437 | A1 | 10/2013 | Boylan et al. |

FOREIGN PATENT DOCUMENTS

| | | | |
|---|---|---|---|
| CN | 108431028 | A | 8/2018 |
| EP | 2932966 | A1 | 10/2015 |
| WO | 2004069826 | A1 | 8/2004 |
| WO | 2015120065 | A1 | 8/2015 |

OTHER PUBLICATIONS

Bi, Pengpeng, et al., "Inhibition of Notch signaling promotes browning of white adipose tissue and ameliorates obesity", Nature Medicine, Aug. 2014, vol. 20, No. 8, 10 pages.

(Continued)

*Primary Examiner* — Savitha M Rao
(74) *Attorney, Agent, or Firm* — Reichel Stohry Dean LLP; Natalie J. Dean

(57) ABSTRACT

Provided is the use of Notch signaling inhibitors such as γ-secretase inhibitors (GSIs), which increase expression of uncoupling protein-1 (UCP-1), to selectively increase browning of white adipose tissue, for example, in the treatment of obesity and metabolic disorders such as type 2 diabetes mellitus (T2DM), fatty liver disease, atherosclerosis, and others, including comorbidities thereof.

18 Claims, 13 Drawing Sheets

Specification includes a Sequence Listing.

(51) Int. Cl.

| | |
|---|---|
| ***A61K 31/19*** | (2006.01) |
| ***A61K 31/192*** | (2006.01) |
| ***A61K 31/417*** | (2006.01) |
| ***A61K 31/4245*** | (2006.01) |
| ***A61P 3/08*** | (2006.01) |

(52) U.S. Cl.
CPC ........ *A61K 31/417* (2013.01); *A61K 31/4245* (2013.01); *A61P 3/08* (2018.01)

(58) Field of Classification Search
CPC ................ A61K 31/4245; A61K 31/55; A61K 31/5513; A61K 9/1647; A61K 9/19; A61K 9/5153; A61P 3/04; A61P 3/08; C12N 2501/105; C12N 2501/42; C12N 2503/02; C12N 2533/40; C12N 5/0653
See application file for complete search history.

(56) References Cited

OTHER PUBLICATIONS

Huang, Di, et al., "In Vitro Evaluation of Clinical Candidates of y-Secretase Inhibitors: Effects on Notch Inhibition and Promoting Beige Adipogenesis and Mitochondrial Biogenesis", Pharm Res, (2020), vol. 37, No. 185, 13 pages.
Jiang, Chunhui, et al., "Dibenzazepine-Loaded Nanoparticles Induce Local Browning of White Adipose Tissue to Counteract Obesity", Molecular Therapy, July 2017Vol. 25, No. 7, pp. 1718-1729.
European Search Report, Application No. EP21846580.5, mailed Oct. 9, 2024, 21 pages.
International Search Report and Written Opinion, issued by the ISA/US for International Patent Application No. PCT/US2021/042867, pp. 1-11, mailed Dec. 30, 2021.
Bi et al., "Notch Signaling Regulates Adipogenesis and Energy Metabolism," entire document especially p. viii, Para 1; p. 29, Para 3; p. 45, Para 1, pp. 1-50, Jan. 1, 2015.

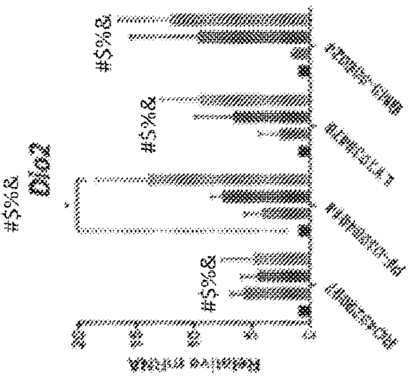
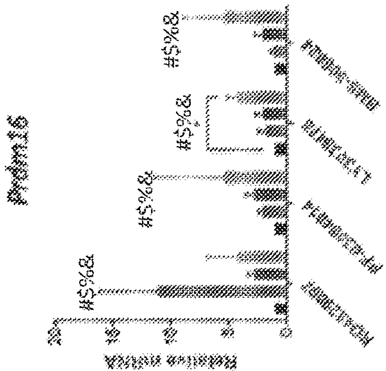
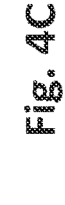
Fig. 4C
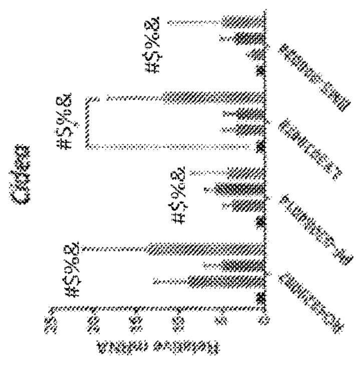
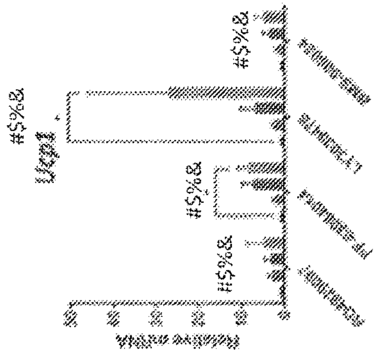

NOTCH SIGNALING INHIBITORS FOR TREATING OBESITY AND METABOLIC DISORDERS

CROSS REFERENCE TO RELATED APPLICATIONS

This present U.S. patent application is a national stage entry under 35 U.S.C. § 371 (b) of International Application No. PCT/US2021/042867, filed on Jul. 23, 2021, which is related to and claims the priority benefit of U.S. Provisional Patent Application No. 63/055,410, filed Jul. 23, 2020, the contents of which are hereby incorporated by reference in their entirety into this disclosure.

GOVERNMENT SUPPORT

This disclosure was made with government support under DK115277 and CA212609 awarded by the National Institutes of Health. The government has certain rights in the disclosure.

STATEMENT OF SEQUENCE LISTING

A computer-readable form (CRF) of the Sequence Listing is submitted concurrently with this application. The file, entitled 69133-02_Seq_Listing_ST25_txt, is generated on May 5, 2021. Applicant states that the content of the computer-readable form is the same and the information recorded in computer readable form is identical to the written sequence listing.

TECHNICAL FIELD

The present disclosure relates to the use of Notch signaling inhibitors such as γ-secretase inhibitors (GSIs), which increase expression of uncoupling protein-1 (UCP-1), to selectively increase browning of white adipose tissue, for example, in the treatment of obesity and metabolic disorders such as type 2 diabetes mellitus (T2DM), fatty liver disease, atherosclerosis, and others, including comorbidities thereof.

BACKGROUND

Type 2 diabetes mellitus (T2DM) and obesity are closely linked metabolic disorders responsible for a significant amount of excess morbidity and mortality. Obesity is a chronic disease that is strongly associated with a reduction in life expectancy and an increase in mortality from cardiovascular disease, diabetes, cancer, and other causes. Current estimates show that over 50% of the world's population will be overweight or obese by the year 2030 if the trends continue W. Excess white adipose tissue (WAT) in obese individuals accumulates in muscle and liver, among numerous other locations, producing insulin resistance through both endocrine and paracrine mechanisms. In susceptible people, the increased demand this insulin resistance places upon the pancreas eventually leads to its failure to produce sufficient insulin to maintain blood sugar in a normal range and T2DM results. Increasingly, medications are being developed that treat both obesity and T2DM, with liraglutide (brand names SAXENDA® for obesity and VICTOZA® for T2DM) being the most prominent example Understanding the processes and metabolic perturbations that contribute to WAT accumulation in obesity is particularly important for the development of therapeutic strategies for both obesity and T2DM. WAT produces multiple adipokines and inflammatory mediators that foster insulin resistance (Ouchi et al., Nature Reviews Immunol. 11: 85-97, 2011). In contrast, brown adipocytes found in brown adipose tissues (BAT) can break down and utilize lipids to generate heat via uncoupling protein 1 (UCP1)-mediated thermogenesis, which is associated with a healthier metabolic phenotype [2]. Thermogenic adipocytes can also be found in certain WAT depots and their presence is dynamically regulated by intrinsic factors and external stimuli. This type of adipocytes is often called beige (or "brite", for brown-in-white) adipocytes and the transformation of white adipocytes to beige adipocytes is termed 'browning' or 'beiging'.

Recent findings in the persistence of brown and beige adipocytes in adult humans suggest that the activation of classical browning process of WAT could be an alternative strategy to increase energy expenditure for the treatment of obesity and metabolic disease [3][4].

SUMMARY

In some aspects, the present disclosure provides a method of increasing browning of white adipose tissue in a subject in need thereof, comprising administering to the subject a Notch signaling inhibitor compound that increases expression of uncoupling protein-1 (UCP-1).

In some aspects, the present disclosure provides a method of treating obesity, including a comorbidity thereof, comprising administering to the subject a Notch signaling inhibitor compound that increases expression of uncoupling protein-1 (UCP-1).

In some aspects, the present disclosure provides a method of treating a metabolic disorder in a subject in need thereof, comprising administering to the subject a Notch signaling inhibitor compound that increases expression of UCP-1, and which, for example, increases browning of white adipose tissue in the subject In some aspects, the present disclosure provides a pharmaceutical composition for use in increasing browning of white adipose tissue in a subject in need thereof, comprising a Notch signaling inhibitor compound that increases expression of uncoupling protein-1 (UCP-1).

In some aspects, the present disclosure provides a particle (e.g., a nanoparticle or microparticle), comprising a Notch inhibitor compound or a derivative, prodrug, or pharmaceutically acceptable salt thereof, and a biodegradable polymer.

In some aspects, the present disclosure provides a particle formulation comprising a Notch inhibitor compound or a derivative, prodrug, or pharmaceutically acceptable salt thereof, and a biodegradable polymer.

In some aspects, the present disclosure provides a nanoparticle formulation comprising a γ-secretase inhibitor (GSI) or a derivative, prodrug, or pharmaceutically acceptable salt thereof, and poly-D-L-lactide-co-glycolide (PLGA), wherein the nanoparticle has an average diameter of from about 150 nm to about 200 nm.

In some aspects, the present disclosure provides a microparticle formulation comprising a γ-secretase inhibitor (GSI) or a derivative, prodrug, or pharmaceutically acceptable salt thereof, and poly-D-L-lactide-co-glycolide (PLGA), wherein the microparticle has an average diameter of from about 50 μm to about 150 μm.

In some embodiments, the subject has, or is at risk for developing, obesity including a comorbidity thereof. In certain embodiments, the subject has, or is at risk for developing, a metabolic disorder. Also included are methods of treating obesity including a comorbidity thereof, and/or treating a metabolic disorder, in a subject in need thereof, comprising administering to the subject a Notch signaling inhibitor compound that increases expression of uncoupling protein-1 (UCP-1), and which optionally increases browning of white adipose tissue in the subject.

In some embodiments, the comorbidity of obesity, and/or the metabolic disorder, are selected from one or more of type 2 diabetes mellitus (T2DM), insulin resistance, prediabetes, hyperlipidemia, fatty liver disease optionally nonalcoholic steatohepatitis (NASH), cardiovascular disease, atherosclerosis, obstructive sleep apnea, asthma, and osteoarthritis. In some embodiments, the subject has metabolic syndrome. In some embodiments, the metabolic syndrome comprises any combination of abdominal obesity, high blood pressure, high blood sugar optionally T2DM, high serum triglycerides, and low serum high-density lipoprotein (HDL). In some embodiments, the subject has a body mass index (BMI) of about or at least about 25, 30, 35, or 40 $kg/m^2$. In some embodiments, the subject has class I obesity (BMI of about 30-35 $kg/m^2$), class II obesity (BMI of about 35-40 $kg/m^2$), or class III obesity (BMI greater than about 40 $kg/m^2$). In some embodiments, the subject has fasting glucose levels of about or at least about 100 mg/dL. In some embodiments, the subject has fasting glucose levels of about 100-125 mg/dL (prediabetes), or about 126 mg/dL or higher (diabetes).

In some embodiments, the compound is a γ-secretase inhibitor (GSI), or a derivative, prodrug, or pharmaceutically acceptable salt thereof. In some embodiments, the GSI is a compound selected from Table 1, or a derivative, prodrug, or pharmaceutically acceptable salt thereof.

In some embodiments, the compound is formulated as microparticles or nanoparticles (e.g., the microparticles or nanoparticles as described herein). In some embodiments, the compound is formulated with a biodegradable polymer, and is optionally formulated as biodegradable polymer-based nanoparticles or microparticles, optionally composed of poly-lactic acid (PLA), poly-D-L-glycolide (PLG), poly-D-L-lactide-co-glycolide (PLGA), polycaprolactone (PCL), poly(trimethylene carbonate) (PTMC), polydioxanone (PDS), poly(ortho-ester), polyanhydrides, poly(anhydride-co-imide), poly(anhydride-esters), polyurethanes, poly (glycerol sebacate), poly(ethylene imine), poly(acrylic acid) (PAA), polyethylene glycol (PEG), poly(vinyl alcohol) (PVA), poly(N-isopropylacrylamide) (PNIPAm), poly(oxazolines), oligo(ethylene glycol) fumarates (OPFs), polyacrylic amide, synthetic poly(amino acids), polyphosphazenes, poly(phosphoesters), poly(propylene fumarate), collagen, polyphosphazenes, polyanhydrides, poly(amino acids), polyhydroxyalkanoates, polydioxanone (PDO), polysaccharides (optionally, hyaluronic acid, chitosan, dextran, chondroitin sulfate, alginate, and/or cellulose), and/or polycyanoacrylate (PCA).

Certain embodiments comprise directly administering the compound to the subject at a site, or proximal to a site, which contains the white adipose tissue.

Some embodiments increase expression of UCP-1, including in the white adipose tissue, by about or at least about 2, 5, 10, 50, 100, 500, or 1000-fold relative to a baseline reference or control. Some embodiments increase browning of white adipose tissue in the subject by about or at least about 5, 10, 20, 30, 40, 50, 60, 70, 80, 90, or 100%, relative to a baseline reference or control. Some embodiments reduce white adipose tissue in the subject, for example, by about or at least about 5, 10, 20, 30, 40, or 50% or more, relative to a baseline reference or control. Some embodiments reduce body weight in the subject, for instance, by about or at least about 5, 10, 20, 30, 40, or 50% or more, relative to a baseline reference or control, or optionally by about or at least about 5, 10, 20, 30, 40, 50, 60, 70, 80, 90, or 100 kg or more.

Certain embodiments reduce body mass index (BMI) in the subject, for example, by about or at least about 1, 2, 3, 4, 5, 6, 7, 8, 9, 10, 11, 12, 13, 14, 15, 16, 17, 18, 19, or 20 $kg/m^2$. In particular embodiments, the reduced body weight and/or reduced BMI in the subject is maintained for about or at least about 1, 2, 3, 4, 5, 6, 7, 8, 9, or 10 years or more.

Certain embodiments improve glucose homeostasis in the subject, for example, wherein the subject has prediabetes or T2DM. Certain embodiments reduce levels of fasting glucose in the subject, optionally by about or at least about 10, 20, 30, 40, or 50% or more, relative to a baseline reference or control, optionally to a level of about or less than about 100 mg/dL. Certain embodiments increase glucose tolerance in the subject, for example, by about or at least about 10, 20, 30, 40, or 50% or more, relative to a baseline reference or control, optionally to a level of about or less than about 140 mg/dL, as measured in an oral glucose tolerance test. Certain embodiments increase life expectancy in the subject, for instance, by about or at least about 1, 2, 3, 4, 5, 6, 7, 8, 9, 10, 11, 12, 13, 14, 15, 16, 17, 18, 19, or 20 years or more.

Some embodiments include pharmaceutical compositions for use in treating obesity, including a comorbidity thereof, and/or for treating a metabolic disorder, comprising a Notch signaling inhibitor compound that increases expression of UCP-1. Certain embodiments include the use of a composition in the preparation of a medicament for increasing browning of white adipose tissue in a subject in need thereof, comprising a Notch signaling inhibitor compound that increases expression of UCP-1. Some embodiments include the use of a composition in the preparation of a medicament for treating obesity, including a comorbidity thereof, and/or for treating a metabolic disorder, comprising a Notch signaling inhibitor compound that increases expression of UCP-1. In certain pharmaceutical compositions or uses, the Notch signaling inhibitor compound is a γ-secretase inhibitor (GSI), or a derivative, prodrug, or pharmaceutically acceptable salt thereof. In some embodiments, the GSI is a compound selected from Table 1, or a derivative, prodrug, or pharmaceutically acceptable salt thereof.

BRIEF DESCRIPTION OF THE DRAWINGS

(FIG. 1A) Real-time qPCR analysis showing the mRNA levels of the Notch target gene Hes1 in 3T3-L1 preadipocytes after 12 h treatments with seven GSIs at a concentration of 1 μM; (FIG. 1B) Real-time qPCR analysis showing the mRNA levels of Hes1 in 3T3-L1 preadipocytes after 12 h treatments with four most efficient GSIs at concentrations of 0, 0.5, 1, and 10 μM. *$p<0.05$, $p<0.01$, *$p<0.005$ and ****$p<0.001$ (One-way or two-way ANOVA followed by Tukey's multiple comparison test). Data are shown as mean±SEM. n=3 individual experiments.

(FIG. 3A) Representative phase contrast and bright field images of differentiated 3T3-L1 cells stained with Oil Red 0 after the treatment with GSIs at the concentration of 1 μM; (FIG. 3B) Relative absorbance at 500 nm of cell lysates extracted from Oil Red 0 stained cells treated with different concentrations of GSIs. *$p<0.05$, $p<0.01$, *$p<0.005$ and ****$p<0.001$ (Two-way ANOVA followed by Tukey's multiple comparison test). Data are shown as mean±SEM. n=3 individual experiments.

FIGS. 4A-4E shows that GSIs upregulate the expression of beige adipogenic and browning marker genes in differentiated 3T3-L1 cells. (FIGS. 4A-4C) Real-time qPCR analysis showing the relative mRNA levels of adipogenic genes, including Fabp4 and Ppargcα (FIG. 4A), mitochondrial and beige cell surface marker genes, including Cox5B and Tmem26 (FIG. 4B), and browning marker genes, including Ucp1, Cidea, Prdm16, and Dio2 (FIG. 4C); (FIG. 4D) Western blot results showing relative protein abundance of UCP1, PPARγ, and C/EBPα in differentiated 3T3-L1 cells treated with GSIs at three concentrations; (FIG. 4E) Quantification of the relative protein levels of UCP1, PPARγ, and C/EBPα normalized to β-Actin controls by densitometry analysis. *$p<0.05$, $p<0.01$, *$p<0.005$ and ****$p<0.001$ (Two-way ANOVA followed by Tukey's multiple comparison test). Data are shown as mean±SEM. n=3 individual experiments.

(FIG. 7B) PF-03084014-PLGA NPs; (FIG. 7C) LY3039478-PLGA NPs; and (FIG. 7D) BMS-906024-PLGA NPs were measured.

DETAILED DESCRIPTION

Definitions

Figure 1B:
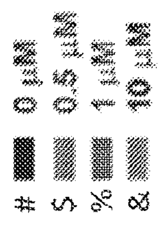
FIGS. 1A-1B show the effects of GSIs on Notch inhibition.
Figure 1B:
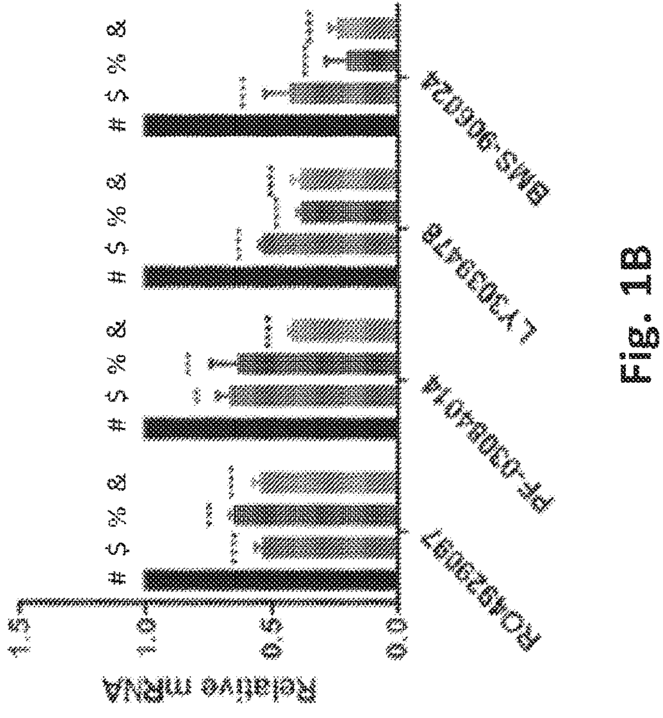

Unless defined otherwise, all technical and scientific terms used herein have the same meaning as commonly understood by those of ordinary skill in the art to which the disclosure belongs. Although any methods, materials, compositions, reagents, cells, similar or equivalent similar or equivalent to those described herein can be used in the practice or testing of the subject matter of the present disclosure, preferred methods and materials are described. All publications and references, including but not limited to patents and patent applications, cited in this specification are herein incorporated by reference in their entirety as if each individual publication or reference were specifically and individually indicated to be incorporated by reference herein as being fully set forth. Any patent application to which this application claims priority is also incorporated by reference herein in its entirety in the manner described above for publications and references.

Standard techniques may be used for recombinant DNA, oligonucleotide synthesis, and tissue culture and transformation (e.g., electroporation, lipofection). Enzymatic reactions and purification techniques may be performed according to manufacturer's specifications or as commonly accomplished in the art or as described herein. These and related techniques and procedures may be generally performed according to conventional methods well known in the art and as described in various general and more specific references that are cited and discussed throughout the present specification. Unless specific definitions are provided, the nomenclature utilized in connection with, and the laboratory procedures and techniques of, molecular biology, analytical chemistry, synthetic organic chemistry, and medicinal and pharmaceutical chemistry described herein are those well-known and commonly used in the art. Standard techniques may be used for recombinant technology, molecular biological, microbiological, chemical syntheses, chemical analyses, pharmaceutical preparation, formulation, and delivery, and treatment of patients.

For the purposes of the present disclosure, the following terms are defined below.

The articles "a" and "an" are used herein to refer to one or to more than one (i.e., to at least one) of the grammatical object of the article. By way of example, "an element" includes "one element", "one or more elements" and/or "at least one element".

By "about" is meant a quantity, level, value, number, frequency, percentage, dimension, size, amount, weight or length that varies by as much as 20, 15, 10, 9, 8, 7, 6, 5, 4, 3, 2 or 1% to a reference quantity, level, value, number, frequency, percentage, dimension, size, amount, weight or length.

An "antagonist" or "inhibitor" refers to biological structure or chemical agent that interferes with or otherwise reduces the physiological action of another agent or molecule. In some instances, the antagonist or inhibitor specifically binds to the other agent or molecule. Included are full and partial antagonists/inhibitors.

An "agonist" refers to biological structure or chemical agent that increases or enhances the physiological action of another agent or molecule. In some instances, the agonist specifically binds to the other agent or molecule. Included are full and partial agonists.

As used herein, a subject "at risk" of developing a disease, or adverse reaction may or may not have detectable disease, or symptoms of disease, and may or may not have displayed detectable disease or symptoms of disease prior to the treatment methods described herein. "At risk" denotes that a subject has one or more risk factors, which are measurable parameters that correlate with development of a disease, as described herein and known in the art. A subject having one or more of these risk factors has a higher probability of developing disease, or an adverse reaction than a subject without one or more of these risk factor(s).

"Biocompatible" refers to materials or compounds which are generally not injurious to biological functions of a cell or subject and which will not result in any degree of unacceptable toxicity, including allergenic and disease states.

The term "binding" refers to a direct association between two molecules, due to, for example, covalent, electrostatic, hydrophobic, and ionic and/or hydrogen-bond interactions, including interactions such as salt bridges and water bridges.

Throughout this disclosure, unless the context requires otherwise, the words "comprise," "comprises," and "comprising" will be understood to imply the inclusion of a stated step or element or group of steps or elements but not the exclusion of any other step or element or group of steps or elements.

By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they materially affect the activity or action of the listed elements.

The term "endotoxin free" or "substantially endotoxin free" relates generally to compositions, solvents, and/or vessels that contain at most trace amounts (e.g., amounts having no clinically adverse physiological effects to a subject) of endotoxin, and preferably undetectable amounts of endotoxin. Endotoxins are toxins associated with certain micro-organisms, such as bacteria, typically gram-negative bacteria, although endotoxins may be found in gram-positive bacteria, such as *Listeria monocytogenes*. The most prevalent endotoxins are lipopolysaccharides (LPS) or lipo-oligo-saccharides (LOS) found in the outer membrane of various Gram-negative bacteria, and which represent a central pathogenic feature in the ability of these bacteria to cause disease. Small amounts of endotoxin in humans may produce fever, a lowering of the blood pressure, and activation of inflammation and coagulation, among other adverse physiological effects.

Therefore, in pharmaceutical production, it is often desirable to remove most or all traces of endotoxin from drug products and/or drug containers, because even small amounts may cause adverse effects in humans. A depyrogenation oven may be used for this purpose, as temperatures in excess of 300° C. are typically required to break down most endotoxins. For instance, based on primary packaging material such as syringes or vials, the combination of a glass temperature of 250° C. and a holding time of 30 minutes is often sufficient to achieve a 3 log reduction in endotoxin levels. Other methods of removing endotoxins are contemplated, including, for example, chromatography and filtration methods, as described herein and known in the art.

Endotoxins can be detected using routine techniques known in the art. For example, the Limulus Amoebocyte Lysate assay, which utilizes blood from the horseshoe crab, is a very sensitive assay for detecting presence of endotoxin. In this test, very low levels of LPS can cause detectable coagulation of the limulus lysate due a powerful enzymatic cascade that amplifies this reaction. Endotoxins can also be quantitated by enzyme-linked immunosorbent assay (ELISA). To be substantially endotoxin free, endotoxin levels may be less than about 0.001, 0.005, 0.01, 0.02, 0.03, 0.04, 0.05, 0.06, 0.08, 0.09, 0.1, 0.5, 1.0, 1.5, 2, 2.5, 3, 4, 5, 6, 7, 8, 9, or 10 EU/mg of active compound. Typically, 1 ng lipopolysaccharide (LPS) corresponds to about 1-10 EU.

The term "half maximal effective concentration" or "$EC_{50}$" refers to the concentration of an agent (e.g., Notch signaling inhibitor, γ-secretase inhibitor) as described herein at which it induces a response halfway between the baseline and maximum after some specified exposure time; the $EC_{50}$ of a graded dose response curve therefore represents the concentration of a compound at which 50% of its maximal effect is observed. $EC_{50}$ also represents the plasma concentration required for obtaining 50% of a maximum effect in vivo. Similarly, the "$EC_{90}$" refers to the concentration of an agent or composition at which 90% of its maximal effect is observed. The "$EC_{90}$" can be calculated from the "$EC_{50}$" and the Hill slope, or it can be determined from the data directly, using routine knowledge in the art. In some embodiments, the $EC_{50}$ of an agent (e.g., Notch signaling inhibitor, γ-secretase inhibitor) is less than about 0.01, 0.05, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 25, 30, 40, 50, 60, 70, 80, 90, 100, 200 or 500 nM. In some embodiments, an agent will have an $EC_{50}$ value of about 1 nM or less.

The "half-life" of an agent (e.g., Notch signaling inhibitor, γ-secretase inhibitor) refers to the time it takes for the agent to lose half of its pharmacologic, physiologic, or other activity, relative to such activity at the time of administration into the serum or tissue of an organism, or relative to any other defined time-point. "Half-life" can also refer to the time it takes for the amount or concentration of an agent to be reduced by half of a starting amount administered into the serum or tissue of an organism, relative to such amount or concentration at the time of administration into the serum or tissue of an organism, or relative to any other defined time-point. The half-life can be measured in serum and/or any one or more selected tissues.

The terms "modulating" and "altering" include "increasing," "enhancing" or "stimulating," as well as "decreasing" or "reducing," typically in a statistically significant or a physiologically significant amount or degree relative to a control. An "increased," "stimulated" or "enhanced" amount is typically a "statistically significant" amount, and may include an amount that is about or at least about 1.1, 1.2, 1.5, 2, 3, 4, 5, 6, 7, 8, 9, 10, 15, 20, 30, 40, 50, 60, 70, 80, 90, 100, 200, 300, 400, 500, 600, 700, 800, 900, 1000, 2000, 3000, 4000, 5000-fold or more of the amount produced by no composition or a control composition (e.g., the absence of agent or a different agent). An "increased," "stimulated" or "enhanced" amount may also include an amount that is about or at least about 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, 100%, 200%, 300%, 400%, 500%, 600%, 700%, 800%, 900%, 1000%, 2000%, 3000%, 4000%, 5000% or more of the amount produced by no composition or a control composition. A "decreased" or "reduced" amount is typically a "statistically significant"

amount, and may include an amount that is about or at least about 1.1, 1.2, 1.5, 2, 3, 4, 5, 6, 7, 8, 9, 10, 15, 20, 30, 40, 50, 60, 70, 80, 90, 100, 200, 300, 400, 500, 600, 700, 800, 900, 1000, 2000, 3000, 4000, or 5000-fold less of the amount produced by no composition or a control composition. A "decreased" or "reduced" amount may also include a 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100%, 200%, 300%, 400%, 500%, 600%, 700%, 800%, 900%, 1000%, 2000%, 3000%, 4000%, or 5000% less of the amount produced by no composition or a control composition. Examples of comparisons and "statistically significant" amounts are described herein.

"Prodrug" is meant to indicate a compound that may be converted under physiological conditions or by solvolysis to a biologically active compound described herein, for example, a GSI compound. Thus, the term "prodrug" refers to a metabolic precursor of a compound that is pharmaceutically acceptable. A prodrug may be inactive when administered to a subject in need thereof, but is converted in vivo to an active compound. Prodrugs may be rapidly transformed in vivo to yield the parent compound, for example, by hydrolysis in blood. The prodrug compound often offers advantages of solubility, tissue compatibility or delayed release in a mammalian organism (see, Bundgard, H., Design of Prodrugs (1985), pp. 7-9, 21-24 (Elsevier, Amsterdam)). A discussion of prodrugs is provided in Higuchi, T., et al., A.C.S. Symposium Series, Vol. 14, and in Bioreversible Carriers in Drug Design, Ed. Edward B. Roche, American Pharmaceutical Association and Pergamon Press, 1987. Examples of prodrugs include, but are not limited to, acetate, formate, and benzoate derivatives of alcohol or amide derivatives of amine functional groups in the compounds of the disclosure and the like.

The term "prodrug" is also meant to include any covalently bonded carriers, which release the active compound in vivo when such prodrug is administered to a subject. Prodrugs of a compound may be prepared by modifying functional groups present in the compound in such a way that the modifications are cleaved, either in routine manipulation or in vivo, to the parent compound. Prodrugs include compounds where a hydroxy, amino, or mercapto group is bonded to any group that, when the prodrug of the compound is administered to a subject, cleaves to form a free hydroxy, free amino, or free mercapto group, respectively.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier, for example, which has been approved by the United States Food and Drug Administration as being acceptable for use in humans or domestic animals.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

As used herein, the term "solvate" refers to an aggregate that comprises one or more molecules of a compound described herein with one or more molecules of solvent. The solvent may be water, in which case the solvate may be a hydrate. Alternatively, the solvent may be a biologically inert organic solvent. Thus, the compounds described herein may exist as a hydrate, including a monohydrate, dihydrate, hemihydrate, sesquihydrate, trihydrate, tetrahydrate and the like, as well as the corresponding solvated forms. The compound of the disclosure may be true solvates, while in other cases, the compound may merely retain adventitious water or be a mixture of water plus some adventitious solvent.

A "pharmaceutical composition" refers to a formulation of a compound described herein and a medium generally accepted in the art for the delivery of the biologically active compound to mammals, e.g., humans. Such a medium includes all pharmaceutically acceptable carriers, diluents or excipients therefor.

The compounds described herein, or their pharmaceutically acceptable salts, may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present disclosure is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centres of geometric asymmetry, and unless specified otherwise, it is intended that the compounds include both E and Z geometric isomers. Likewise, all tautomeric forms are also intended to be included.

In certain embodiments, the "purity" of any given agent (e.g., Notch signaling inhibitor, γ-secretase inhibitor) in a composition may be defined. For instance, certain compositions may comprise an agent that is at least 80%, 85%, 90%, 91%, 92%, 93%, 94%, 95%, 96%, 97%, 98%, 99%, or 100% pure on a weight-weight basis, including all decimals and ranges in between, as measured, for example and by no means limiting, by high performance liquid chromatography (HPLC), a well-known form of column chromatography used frequently in biochemistry and analytical chemistry to separate, identify, and quantify compounds.

The term "solubility" refers to the property of an agent (e.g., Notch signaling inhibitor, γ-secretase inhibitor) provided herein to dissolve in a liquid solvent and form a homogeneous solution. Solubility is typically expressed as a concentration, either by mass of solute per unit volume of solvent (g of solute per kg of solvent, g per dL (100 mL), mg/ml, etc.), molarity, molality, mole fraction or other similar descriptions of concentration. The maximum equilibrium amount of solute that can dissolve per amount of solvent is the solubility of that solute in that solvent under the specified conditions, including temperature, pressure, pH, and the nature of the solvent. In certain embodiments, solubility is measured at physiological pH, or other pH, for example, at pH 5.0, pH 6.0, pH 7.0, pH 7.4, pH 7.6, pH 7.8, or pH 8.0 (e.g., about pH 5-8). In certain embodiments, solubility is measured in water or a physiological buffer such as PBS or NaCl (with or without $NaPO4$). In specific embodiments, solubility is measured at relatively lower pH (e.g., pH 6.0) and relatively higher salt (e.g., 500 mM NaCl and 10 mM $NaPO4$). In certain embodiments, solubility is measured in a biological fluid (solvent) such as blood or serum. In certain embodiments, the temperature can be about room temperature (e.g., about 20, 21, 22, 23, 24, 25° C.) or about body temperature (37° C.). In certain embodiments, an agent has a solubility of at least about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 25, 30, 40, 50, 60, 70, 80, 90 or 100 mg/ml at room temperature or at 37° C.

"Stable compound" and "stable structure" are meant to indicate a compound that is sufficiently robust to survive isolation to a useful degree of purity from a reaction mixture, and formulation into a therapeutic agent.

By "statistically significant," it is meant that the result was unlikely to have occurred by chance. Statistical significance can be determined by any method known in the art. Commonly used measures of significance include the p-value, which is the frequency or probability with which the observed event would occur, if the null hypothesis were true. If the obtained p-value is smaller than the significance level, then the null hypothesis is rejected. In simple cases, the significance level is defined at a p-value of 0.05 or less.

A "subject" or a "subject in need thereof" or a "patient" or a "patient in need thereof" includes a mammalian subject such as a human subject.

"Substantially" or "essentially" includes nearly totally or completely, for instance, 95%, 96%, 97%, 98%, 99% or greater of some given quantity.

A "stereoisomer" refers to a compound made up of the same atoms bonded by the same bonds but having different three-dimensional structures, which are not interchangeable. The present disclosure includes various stereoisomers and mixtures thereof and includes "enantiomers", which refers to two stereoisomers whose molecules are nonsuperimposeable mirror images of one another.

A "tautomer" refers to a proton shift from one atom of a molecule to another atom of the same molecule. The present disclosure includes tautomers of any said compounds.

As used herein, the terms "therapeutically effective amount", "therapeutically effective dose", "therapeutic dose," or "prophylactically effective amount" is the amount of an agent (e.g., Notch signaling inhibitor, γ-secretase inhibitor, additional agent) needed to elicit the desired biological response following administration.

As used herein, "treatment" of a subject (e.g., a mammal, such as a human) or a cell is any type of intervention used in an attempt to alter the natural course of the individual or cell. Treatment includes, but is not limited to, administration of at least one pharmaceutical composition, and may be performed either prophylactically or subsequent to the initiation of a pathologic event or contact with an etiologic agent. Also included are "prophylactic" treatments, which can be directed to reducing the rate of progression of the disease or condition being treated, delaying the onset of that disease or condition, or reducing the severity of its onset. "Treatment" or "prophylaxis" does not necessarily indicate complete eradication, cure, or prevention of the disease or condition, or associated symptoms thereof.

Methods, Particles, and Formulations of the Present Disclosure

In some aspects, the present disclosure provides a method of increasing browning of white adipose tissue in a subject in need thereof, comprising administering to the subject a Notch signaling inhibitor compound that increases expression of uncoupling protein-1 (UCP-1).

In some aspects, the present disclosure provides a method of treating obesity, including a comorbidity thereof, comprising administering to the subject a Notch signaling inhibitor compound that increases expression of uncoupling protein-1 (UCP-1).

In some aspects, the present disclosure provides a method of treating a metabolic disorder in a subject in need thereof, comprising administering to the subject a Notch signaling inhibitor compound that increases expression of UCP-1, and which, for example, increases browning of white adipose tissue in the subject In some aspects, the present disclosure provides a pharmaceutical composition for use in increasing browning of white adipose tissue in a subject in need thereof, comprising a Notch signaling inhibitor compound that increases expression of uncoupling protein-1 (UCP-1).

In some aspects, the present disclosure provides a particle (e.g., a nanoparticle or microparticle), comprising a Notch inhibitor compound or a derivative, prodrug, or pharmaceutically acceptable salt thereof, and a biodegradable polymer.

In some aspects, the present disclosure provides a particle formulation comprising a Notch inhibitor compound or a derivative, prodrug, or pharmaceutically acceptable salt thereof, and a biodegradable polymer.

In some aspects, the present disclosure provides a nanoparticle formulation comprising a γ-secretase inhibitor (GSI) or a derivative, prodrug, or pharmaceutically acceptable salt thereof, and poly-D-L-lactide-co-glycolide (PLGA), wherein the nanoparticle has an average diameter of from about 150 nm to about 200 nm.

In some aspects, the present disclosure provides a microparticle formulation comprising a γ-secretase inhibitor (GSI) or a derivative, prodrug, or pharmaceutically acceptable salt thereof, and poly-D-L-lactide-co-glycolide (PLGA), wherein the microparticle has an average diameter of from about 50 μm to about 150 μm.

Each embodiment in this specification is to be applied to every other embodiment unless expressly stated otherwise.

Embodiments of the present disclosure include methods of inducing or otherwise increasing browning of white adipose tissue in a subject in need thereof, comprising administering to the subject a Notch signaling inhibitor compound that increases expression of uncoupling protein-1 (UCP-1). Also included are methods of treating obesity, including a comorbidity thereof, and/or methods of treating a metabolic disorder in a subject in need thereof, comprising administering to the subject a Notch signaling inhibitor compound that increases expression of UCP-1, and which, for example, increases browning of white adipose tissue in the subject White adipose tissue (WAT) or white fat is one of the two types of adipose tissue found in mammals. WAT is used mainly for energy storage, and also acts as a thermal insulator, helping to maintain body temperature. In contrast, brown adipose tissue actively contributes to thermoregulation, for example, by producing heat via non-shivering thermogenesis. Brown adipocytes contain numerous smaller droplets and a much higher number of (iron-containing) mitochondria, which gives the tissue its color. Brown fat also contains more capillaries than white fat, which supply the tissue with oxygen and nutrients and distribute the produced heat throughout the body. However, thermogenic adipocytes can also be found in certain WAT depots, and their presence is dynamically regulated by intrinsic factors and external stimuli. These types of thermogenic adipocytes are often called beige (or brite, for brown-in-white) adipocytes, and the term "browning" or "beiging", as used herein, refers to the transformation of white adipocytes to thermogenic beige adipocytes.

As noted above, certain compounds inhibit or otherwise reduce Notch signaling. The Notch signaling pathway is a highly conserved cell signaling system. For example, mammals have four different notch receptors, referred to as NOTCH1, NOTCH2, NOTCH3, and NOTCH4. The notch receptor is a single-pass transmembrane receptor protein; including a hetero-oligomer composed of a large extracellular portion, which associates in a calcium-dependent, non-covalent interaction with a smaller piece of the notch protein composed of a short extracellular region, a single transmembrane-pass, and a small intracellular region.

Notch signaling plays a critical role in development and regeneration of stem/progenitor cells as well as in regulation of cell fate [5]. It is known to be an evolutionarily conserved mechanism that balances differentiation and proliferation in several cell types, including muscle stem cells and adipocyte progenitor cells [6][7][8]. Notch signaling is mediated by binding of Delta-like and Serrate/Jagged family ligands with Notch receptors (Notch-1, -2, -3, and -4), leading to γ-secretase-mediated proteolytic cleavage and the release of Notch intracellular domain (NICD). Subsequently, NICD translocates to the nucleus, where it interacts with the recombination signal binding protein for immunoglobulin kappa J region (RBPJ) transcriptional complex to activate the transcription of downstream targets, including HES and HEY family genes, to regulate cell differentiation. Inhibition of Notch signaling can be measured according to routine techniques in the art.

In certain embodiments, a Notch signaling inhibitor compound induces or otherwise increases expression of uncoupling protein-1 (UCP-1), or thermogenin, an uncoupling protein found in the mitochondria of brown adipose tissue (see, for example, UniProt: P25874). UCP-1 is a transmembrane protein that decreases the proton gradient generated in oxidative phosphorylation, for example, by increasing the permeability of the inner mitochondrial membrane, allowing protons that have been pumped into the intermembrane space to return to the mitochondrial matrix. UCP-1 mediated heat generation in brown fat uncouples the respiratory chain, allowing for fast substrate oxidation with a low rate of ATP production. In some embodiments, a Notch signaling inhibitor compound increases expression of UCP-1, for example, in white adipose tissue, by about or at least about 2, 5, 10, 50, 100, 500, or 1000-fold relative to a baseline reference or control.

In some embodiments, as noted above, the subject in need thereof has, or is at risk for developing, obesity, including a comorbidity thereof. In some embodiments, the subject in need thereof has, or is at risk for developing, a metabolic disorder, which can be related or unrelated to obesity. In some embodiments, the comorbidity of obesity, and/or the metabolic disorder, is selected from one or more of type 2 diabetes mellitus (T2DM), hyperlipidemia, insulin resistance, prediabetes, fatty liver disease optionally nonalcoholic steatohepatitis (NASH), cardiovascular disease, atherosclerosis, obstructive sleep apnea, asthma, and osteoarthritis.

In some embodiments, the subject has metabolic syndrome, which refers generally to a combination least three of the five following medical conditions: abdominal obesity, high blood pressure, high blood sugar, high serum triglycerides, and low serum high-density lipoprotein (HDL). Thus, in certain embodiments, the subject has any combination of abdominal obesity, high blood pressure, high blood sugar (for example, T2DM), high serum triglycerides, and low serum HDL. For example, in certain embodiments, a subject is characterized as follows: Central obesity: waist circumference ≥102 cm or 40 inches (male), ≥88 cm or 35 inches (female); dyslipidemia: TG≥1.7 mmol/L (150 mg/dl); dyslipidemia: HDL-C<40 mg/dL (male), <50 mg/dL (female); blood pressure ≥130/85 mmHg (or treated for hypertension); and/or fasting plasma glucose ≥5.6 mmol/L (100 mg/dl), or use of medication for hyperglycemia.

In certain embodiments, a subject is overweight or has, or is at risk for developing, obesity. For instance, in certain embodiments, the subject has a body mass index (BMI) of about or at least about 25, 30, 35, or 40 kg/$m^2$. In specific embodiments, the subject has class I obesity (about 30-35 kg/$m^2$), class II obesity (about 35-40 kg/$m^2$), or class III obesity (greater than about 40 kg/$m^2$).

In some embodiments, a subject has, or is at risk for developing, prediabetes or diabetes, mainly T2DM. For instance, in particular embodiments, the subject has fasting glucose levels of about or at least about 100 mg/dL, including wherein the subject has fasting glucose levels of about 100-125 mg/dL (prediabetes), or about 126 mg/dL or higher (diabetes). In some embodiments, the subject has glucose levels of about or at least about 140 and 199 mg/dL (prediabetes), or about 200 mg/dL or higher (diabetes), as measured after about two hours following an oral glucose tolerance test. In some embodiments, the subject has a random blood sugar level of about 200 mg/dL or higher.

In some embodiments, the Notch signaling inhibitor compound is a γ-secretase inhibitor (GSI), or a derivative, prodrug, or pharmaceutically acceptable salt thereof. Exemplary GSIs are provided in Table 1 below.

TABLE 1

| Exemplary GSIs | | | |
|---|---|---|---|
| Compound Designation | Chemical Structure | Compound Designation | Chemical Structure |
| RO4929097 | 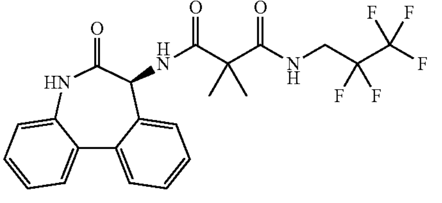 | BMS-708163 | 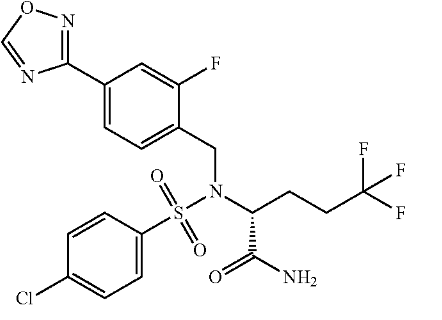 |
| PF-03084014 | 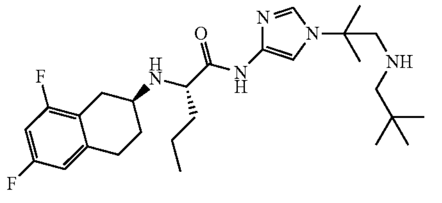 [SMILES: CCC[C@H](N[C@H]1CCc2cc(F)cc(F)c2C1)C(=O)Nc1cn(C(C)(C)CNCC(C)(C)C)cn1] | LY450139 | 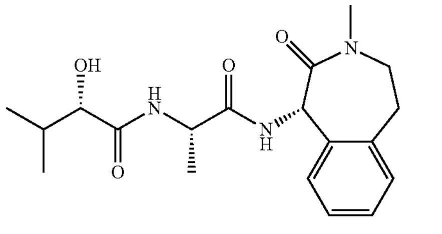 [SMILES: CC(C)[C@H](O)C(=O)N[C@@H](C)C(=O)N[C@@H]1C(=O)N(C)CCc2ccccc21] |
| LY3039478 | 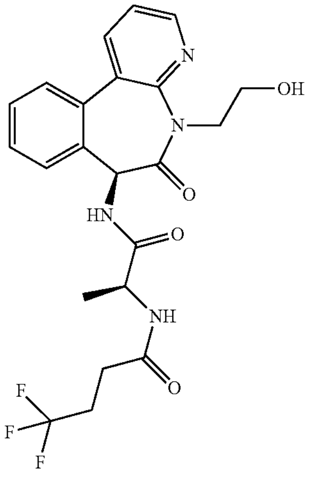 [SMILES: C[C@H](NC(=O)CCC(F)(F)F)C(=O)N[C@@H]1C(=O)N(CCO)c2ncccc2-c2ccccc21] | MK-0752 | 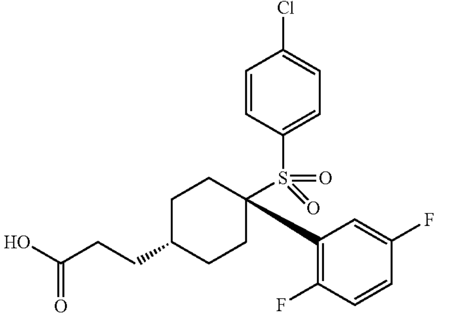 [SMILES: O=C(O)CC[C@H]1CC[C@@](c2cc(F)ccc2F)(S(=O)(=O)c2ccc(Cl)cc2)CC1] |

TABLE 1-continued

| Exemplary GSIs | | | |
|---|---|---|---|
| Compound Designation | Chemical Structure | Compound Designation | Chemical Structure |
| BMS-906024 | 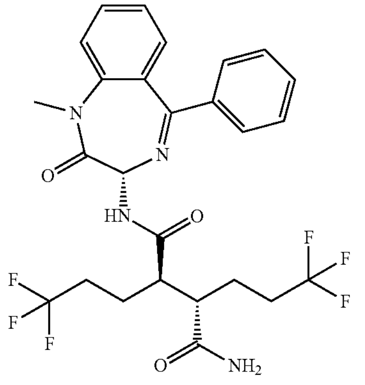 [SMILES: CN1C(=O)[C@@H](NC(=O)[C@H](CCC(F)(F)F)[C@H](CCC(F)(F)F)C(N)=O)N=C(c2ccccc2)c2ccccc21] | | |

Thus, in certain embodiments, a GSI is selected from Table 1, including derivatives, prodrugs, and pharmaceutically acceptable salts thereof.

In some embodiments, the GSI is the malonamide derivative RO4929097 (or RG-4733), or a derivative, prodrug, or pharmaceutically acceptable salt thereof (see, for example, WO 2005/023772 and U.S. Application No. 2005/0054633, which are incorporated by reference for the chemical structures and methods of synthesis related to RO4929097 and derivatives).

In some embodiments, the GSI is a malonamide derivative of Formula I below:

(I)

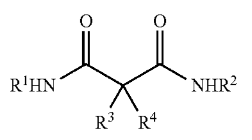

wherein, $R^1$ is one of the following groups:

a)

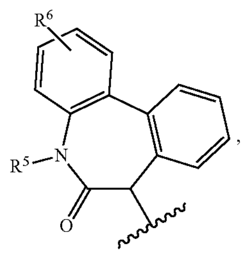

,

-continued b)

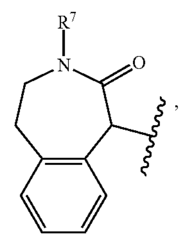

, c)

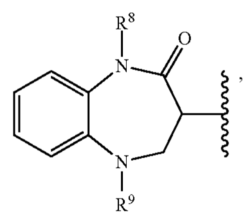

, d)

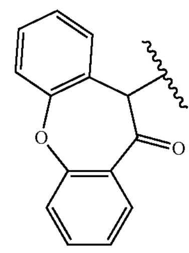

wherein, $R^2$ is lower alkyl, lower alkinyl, $—(CH_2)_n—$O-lower alkyl, $—(CH_2)_n—$S-lower alkyl, $—(CH_2)$, —CN, —(CR'R"), $—CF_3$, —(CR'R"), $—CHF_2$, —(CR'R"), $CH_2F$, $—(CH_2)_n—$C(O)O-lower alkyl, $—(CH_2)_n$-halogen, or is $—(CH_2)_n$-cycloalkyl, optionally substituted by one or more substituents, selected from the group consisting of phenyl, halogen, and $CF_3$;

R', R" are, independently from n and from each other, hydrogen, lower alkyl, lower alkoxy, halogen, or hydroxy;

$R^3$, $R^4$ are, independently from each other, hydrogen, lower alkyl, lower alkoxy, phenyl, or halogen;

$R^5$ is hydrogen, lower alkyl, $—(CH_2)_n—CF_3$, or $—(CH_2)_n$-cycloalkyl;

$R^6$ is hydrogen or halogen;

R is hydrogen or lower alkyl;

R.sup.8 is hydrogen, lower alkyl, lower alkinyl, $—(CH_2)_n—CF_3$, $—(CH_2)_n$-cycloalkyl or, $—(CH_2)_n$-phenyl, optionally substituted by halogen;

$R^9$ is hydrogen, lower alkyl, C(O)H, —C(O)-lower alkyl, —C(O)—$CF_3$, —C(O)—$CH_2F$, —C(O)—$CHF_2$, —C(O)-cycloalkyl, —C(O)—$(CH_2)_n$—O-lower alkyl, —C(O)O—$(CH_2)_n$-cycloalkyl, —C(O)-phenyl, optionally substituted by one or more substituents selected from the group consisting of halogen or —C(O)O-lower alkyl, or is —$S(O)_2$-lower alkyl, —$S(O)_2$—$CF_3$, ~$(CH_2)_n$-cycloalkyl or is —$(CH_2)_n$-phenyl, optionally substituted by halogen;

n is 0, 1, 2, 3 or 4;

including pharmaceutically suitable acid addition salts, optically pure enantiomers, racemates, and diastereomeric mixtures thereof.

As used herein, the term "lower alkyl" denotes a saturated straight- or branched-chain alkyl group containing from 1 to 7 carbon atoms, for example, methyl, ethyl, propyl, isopropyl, n-butyl, i-butyl, 2-butyl, t-butyl, and the like. Preferred lower alkyl groups are groups with 1-4 carbon atoms.

As used herein, the term "lower alkinyl" denotes a unsaturated straight- or branched-carbon chain containing from 2 to 7 carbon atoms and containing at least one triple bond.

The term "cycloalkyl" denotes a saturated carbocyclic group, containing 3-7 carbon atoms.

The term "halogen" denotes chlorine, iodine, fluorine, and bromine.

The term "lower alkoxy" denotes a group wherein the alkyl residues is as defined above, and which is attached via an oxygen atom.

The expression "—$(CR'R")_n$—" may be, for example —$CH_2$—, —$CH_2$—$CH_2$—, —$CH_2$—$CH_2$—$CH_2$—, —$CH_2$—$CF_2$—, —$CH_2$—$CH_2$—$CF_2$—, —$CH_2$—$CH_2$—$CH(OCH_3)$—, —$CH_2CH(OH)$—, or —$C(CH_3)_2$—CH (OH)—.

In some embodiments, the GSI is PF-03084014, or a derivative, prodrug, or pharmaceutically acceptable salt thereof (see, for example, WO 2005/092864 and U.S. Application No. 2005/0215610), which are incorporated by reference for the chemical structures and methods of synthesis related to PF-03084014 and derivatives). In some embodiments, the GSI is LY3039478, or a derivative, prodrug, or pharmaceutically acceptable salt thereof (see, for example, WO 2013/016081 and U.S. Application No. 2013/0029972, which are incorporated by reference for the chemical structures and methods of synthesis related to LY3039478 and derivatives).

In some embodiments, the GSI is the benzodiazepinone compound BMS-906024, or a derivative, prodrug, or pharmaceutically acceptable salt thereof (see, for example, WO 2012/129353 and U.S. Application No. 2014/0357605, which are incorporated by reference for the chemical structures and methods of synthesis related to BMS-906024 and derivatives).

In some embodiments, the GSI is a benzodiazepinone compound of Formula II below:

(II)

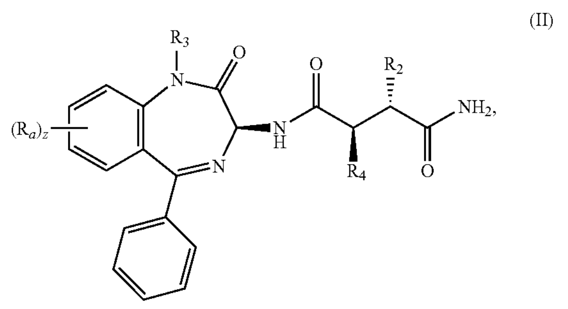

wherein:

$R^1$ is —$CH_2CF_3$ or —$CH_2CH_2CF_2$;

$R^2$ is —$CH_2CF_3$, —$CH_2CH_2CF_3$, or —$CH_2CH_2CH_2CF_3$;

$R^3$ is H or —$CH_3$;

each $R_a$ is independently F, Cl, —CN, —$OCH_3$, and//or —$NHCH_2OCH_3$; and Z is zero, 1, or 2.

In some embodiments, the GSI is BMS-708163, or a derivative, prodrug, or pharmaceutically acceptable salt thereof (see, for example, WO 2009/058552 and U.S. Application No. 2009/0111858, which are incorporated by reference for the chemical structures and methods of synthesis related to BMS-708163 and derivatives). In some embodiments, the GSI is LY450139, or a derivative, prodrug, or pharmaceutically acceptable salt thereof (see, for example, WO 2002/040451 and U.S. Application No. 2004/0248878, which are incorporated by reference for the chemical structures and methods of synthesis related to LY450139 and derivatives). In some embodiments, the GSI is MK-0752, or a derivative, prodrug, or pharmaceutically acceptable salt thereof (see, for example, WO 2002/081435 and U.S. Application No. 2003/0114496, which are incorporated by reference for the chemical structures and methods of synthesis related to MK-0752 and derivatives).

In some embodiments, the compound (e.g., GSI) is formulated as nanoparticles or microparticles. In some embodiments, the compound is formulated with (for example, conjugated to) a biodegradable polymer. For instance, certain compounds are formulated as biodegradable polymer-based nanoparticles or microparticles. The term "nanoparticle" refers to a particle of matter that is about or between about 1-100 nanometers (nm) or so in diameter, and in some instances up to about 500 nm or so. The term "microparticle" refers to a particle of matter that is about or between about 1-1000 μm in diameter or so. In some instances, biodegradable polymer-based nanoparticles or microparticles are composed of poly-lactic acid (PLA), poly-D-L-glycolide (PLG), poly-D-L-lactide-co-glycolide (PLGA), polycaprolactone (PCL), poly(trimethylene carbonate) (PTMC), polydioxanone (PDS), poly(ortho-ester), polyanhydrides, poly(anhydride-co-imide), poly(anhydride-esters), polyurethanes, poly(glycerol sebacate), poly(ethylene imine), poly(acrylic acid) (PAA), polyethylene glycol (PEG), poly(vinyl alcohol) (PVA), poly(N-isopropylacrylamide) (PNIPAm), poly(oxazolines), oligo(ethylene glycol) fumarates (OPFs), polyacrylic amide, synthetic poly(amino acids), polyphosphazenes, poly(phosphoesters), poly(propylene fumarate), collagen, polyphosphazenes, polyanhydrides, poly(amino acids), polyhydroxyalkanoates, polydioxanone (PDO), polysaccharides (for example, hyaluronic acid, chitosan, dextran, chondroitin sulfate, alginate, and/or cellulose), and/or polycyanoacrylate (PCA), including combinations thereof (see, for example, U.S. Application No. 2018/0326080, which is incorporated by reference for polymers; and Mahapatro and Singh, "Biodegradable Nanoparticles Are Excellent Vehicle for Site Directed In-Vivo Delivery of Drugs and Vaccines", J. Nanobiotechnology. 2011, 9:55).

In some embodiments, the particle is a nanoparticle.

In some embodiments, the particle is a microparticle.

In some embodiments, the particle formulation comprises a microparticle or a nanoparticle.

In some embodiments, the particle formulation a microparticle.

In some embodiments, the particle formulation a nanoparticle.

In some embodiments, the nanoparticle has an average diameter of from about 1 nm to about 500 nm, about 5 nm to about 450 nm, about 10 nm to about 400 nm, about 25 nm to about 350 nm, about 50 nm to about 300 nm, about 100 nm to about 250 nm, about 125 nm to about 200 nm, about 150 nm to about 200 nm, about 160 nm to about 185 nm, about 165 nm to about 180 nm, or about 170 nm to about 175 nm.

In some embodiments, the nanoparticle has an average diameter of about 500 nm or less, about 450 nm or less, about 400 nm or less, about 350 nm or less, about 300 nm or less, about 250 nm or less, about 200 nm or less, about 190 nm or less, about 185 nm or less, about 180 nm or less, about 175 nm or less, about 170 nm or less, about 165 nm or less, about 160 nm or less, about 155 nm or less, about 150 nm or less, about 125 nm or less, about 100 nm or less, about 50 nm or less, about 25 nm or less, about 10 nm or less, about 5 nm or less, or about 1 nm or less.

In some embodiments, the nanoparticle has an average diameter of about 170±20 nm, 170±15 nm, about 170±10 nm, about 170±9 nm, about 170±8 nm, about 170±7 nm, about 170±6 nm, about 170±5 nm, about 170±4 nm, about 170±3 nm, about 170±2 nm, about 170±1 nm, about 170±0.5 nm, or about 170±0.1 nm (e.g., about 170 nm).

In some embodiments, the nanoparticle has an average diameter of about 177±20 nm, 177±15 nm, 177±10 nm, about 177±9 nm, about 177±8 nm, about 177±7 nm, about 177±6 nm, about 177±5 nm, about 177±4 nm, about 177±3 nm, about 177±2 nm, about 177±1 nm, about 177±0.5 nm, or about 177±0.1 nm (e.g., about 177 nm).

In some embodiments, the nanoparticle has an average diameter of about 184±20 nm, 184±15 nm, 184±10 nm, about 184±9 nm, about 184±8 nm, about 184±7 nm, about 184±6 nm, about 184±5 nm, about 184±4 nm, about 184±3 nm, about 184±2 nm, about 184±1 nm, about 184±0.5 nm, or about 184±0.1 nm (e.g., about 184 nm).

In some embodiments, the nanoparticle has an average diameter of about 185±20 nm, 185±15 nm, 185±10 nm, about 185±9 nm, about 185±8 nm, about 185±7 nm, about 185±6 nm, about 185±5 nm, about 185±4 nm, about 185±3 nm, about 185±2 nm, about 185±1 nm, about 185±0.5 nm, or about 185±0.1 nm (e.g., about 185 nm).

In some embodiments, the microparticle has an average diameter of from about 500 nm to about 1000 μm, about 1 μm to about 950 μm, about 100 μm to about 900 μm, about 200 μm to about 850 μm, about 300 μm to about 800 μm, about 400 μm to about 750 μm, about 500 μm to about 700 μm, about 550 μm to about 650 μm, or about 600 μm to about 650 μm.

In some embodiments, the microparticle has an average diameter of from about 500 μm to about 700 μm.

In some embodiments, the microparticle has an average diameter of from about 1 μm to about 250 μm, about 10 μm to about 200 μm, about 25 μm to about 175 μm, about 50 μm to about 150 μm, about 75 μm to about 125 μm, or about 100 μm to about 125 μm.

In some embodiments, the microparticle has an average diameter of from about 50 μm to about 150 μm.

In some embodiments, the microparticle has an average diameter of about 1000 μm or less, about 950 μm or less, about 900 μm or less, about 850 μm or less, about 800 μm or less, about 750 μm or less, about 700 μm or less, about 650 μm or less, about 600 μm or less, about 550 μm or less, about 500 μm or less, about 450 μm or less, about 400 μm or less, about 350 μm or less, about 300 μm or less, about 250 μm or less, about 200 μm or less, about 150 μm or less, about 100 μm or less, or about 1 μm or less.

In some embodiments, the microparticle has an average diameter of about 700 μm or less.

In some embodiments, the microparticle has an average diameter of about 200 μm or less.

In some embodiments, the Notch inhibitor compound is a γ-secretase inhibitor (GSI).

In some embodiments, the γ-secretase inhibitor (GSI) is selected from Table 1 and prodrugs thereof.

In some embodiments, the γ-secretase inhibitor (GSI) is selected from Table 1.

In some embodiments, the γ-secretase inhibitor (GSI) is selected from RO4929097, BMS-708163, PF-03084014, LY450139, LY3039478, MK-0752, and BMS-906024, including derivatives, prodrugs, and pharmaceutically acceptable salts thereof.

In some embodiments, the γ-secretase inhibitor (GSI) is selected from RO4929097, BMS-708163, PF-03084014, LY450139, LY3039478, MK-0752, BMS-906024, and prodrugs thereof.

In some embodiments, the γ-secretase inhibitor (GSI) is selected from RO4929097, BMS-708163, PF-03084014, LY450139, LY3039478, MK-0752, and BMS-906024.

In some embodiments, the γ-secretase inhibitor (GSI) is RO4929097 or a prodrug thereof.

In some embodiments, the γ-secretase inhibitor (GSI) is RO4929097.

In some embodiments, the γ-secretase inhibitor (GSI) is a prodrug of RO4929097.

In some embodiments, the γ-secretase inhibitor (GSI) is PF-03084014 or a prodrug thereof.

In some embodiments, the γ-secretase inhibitor (GSI) is PF-03084014.

In some embodiments, the γ-secretase inhibitor (GSI) is a prodrug of PF-03084014.

In some embodiments, the γ-secretase inhibitor (GSI) is LY3039478 or a prodrug thereof.

In some embodiments, the γ-secretase inhibitor (GSI) is LY3039478.

In some embodiments, the γ-secretase inhibitor (GSI) is a prodrug of LY3039478.

In some embodiments, the γ-secretase inhibitor (GSI) is BMS-906024 or a prodrug thereof.

In some embodiments, the γ-secretase inhibitor (GSI) is BMS-906024.

In some embodiments, the γ-secretase inhibitor (GSI) is a prodrug of BMS-906024.

In some embodiments, the particle formulation (e.g., the particle) comprises about 1% to about 50% Notch inhibitor compound by weight, about 1.5% to about 40% Notch inhibitor compound by weight, about 2% to about 30% Notch inhibitor compound by weight, about 2.5% to about 25% Notch inhibitor compound by weight, about 3% to about 20% Notch inhibitor compound by weight, about 4% to about 15% Notch inhibitor compound by weight, or about 5% to about 10% Notch inhibitor compound by weight.

In some embodiments, the particle formulation (e.g., the particle) comprises about 5±2.5% Notch inhibitor compound by weight, about 5±2% Notch inhibitor compound by weight, about 5±1.5% Notch inhibitor compound by weight, about 5±1% Notch inhibitor compound by weight, about 5±0.5% Notch inhibitor compound by weight, about 5±0.1% Notch inhibitor compound by weight (e.g., about 5% Notch inhibitor compound by weight).

In some embodiments, the particle formulation (e.g., the particle) comprises about 10±5% Notch inhibitor compound by weight, about 10±2.5% Notch inhibitor compound by weight, about 10±2% Notch inhibitor compound by weight, about 10±1.5% Notch inhibitor compound by weight, about 10±1% Notch inhibitor compound by weight, about 10±0.5% Notch inhibitor compound by weight, about 10±0.1% Notch inhibitor compound by weight (e.g., about 10% Notch inhibitor compound by weight).

In some embodiments, the particle formulation (e.g., the particle) comprises about 20±10% Notch inhibitor compound by weight, about 20±5% Notch inhibitor compound by weight, about 20±2.5% Notch inhibitor compound by weight, about 20±2% Notch inhibitor compound by weight, about 20±1.5% Notch inhibitor compound by weight, about 20±1% Notch inhibitor compound by weight, about 20±0.5% Notch inhibitor compound by weight, about 20±0.1% Notch inhibitor compound by weight (e.g., about 20% Notch inhibitor compound by weight).

In some embodiments, the formulation is a solution (e.g., a pre-lyophilized solution).

In some aspects, the present disclosure provides a method comprising lyophilizing the formulation described herein (e.g., the pre-lyophilized solution), thereby forming a lyophilized formulation (e.g., lyophilized powder or cake).

In some embodiments, the formulation is a lyophilized formulation (e.g., lyophilized powder or cake).

In some aspects, the present disclosure provides a method comprising adding a solvent to the lyophilized formulation described herein (e.g., lyophilized powder or cake), thereby forming a reconstituted solution.

In some embodiments, the formulation is a reconstituted solution (e.g., of the lyophilized powder or cake).

In some embodiments, the biodegradable polymer is selected from poly-lactic acid (PLA), poly-D-L-glycolide (PLG), poly-D-L-lactide-co-glycolide (PLGA), polycaprolactone (PCL), poly(trimethylene carbonate) (PTMC), polydioxanone (PDS), poly(ortho-ester), polyanhydrides, poly(anhydride-co-imide), poly(anhydride-esters), polyurethanes, poly(glycerol sebacate), poly(ethylene imine), poly (acrylic acid) (PAA), polyethylene glycol (PEG), poly(vinyl alcohol) (PVA), poly(N-isopropylacrylamide) (PNIPAm), poly(oxazolines), oligo(ethylene glycol) fumarates (OPFs), polyacrylic amide, synthetic poly(amino acids), polyphosphazenes, poly(phosphoesters), poly(propylene fumarate), collagen, polyphosphazenes, polyanhydrides, poly(amino acids), polyhydroxyalkanoates, polydioxanone (PDO), polysaccharides (optionally, hyaluronic acid, chitosan, dextran, chondroitin sulfate, alginate, and/or cellulose), and/or polycyanoacrylate (PCA).

In some embodiments, the biodegradable polymer is poly-D-L-lactide-co-glycolide (PLGA).

In some embodiments, the particle formulation comprises a cryoprotectant.

In some embodiments, the cryoprotectant is selected from trehalose, sucrose, fructose, glucose, lactose, mannitol, ribose, maltose, mannose, dextrose, sorbitol, glycine, dextran, gelatine, poly(vinyl pyrrolidone), poly(vinyl alcohol), and aerosil.

In some embodiments, the cryoprotectant is sucrose.

In some aspects, the present disclosure provides a nanoparticle formulation comprising a γ-secretase inhibitor (GSI) or a derivative, prodrug, or pharmaceutically acceptable salt thereof, and poly-D-L-lactide-co-glycolide (PLGA), wherein the nanoparticle has an average diameter of from about 150 nm to about 200 nm.

In some aspects, the present disclosure provides a microparticle formulation comprising a γ-secretase inhibitor (GSI) or a derivative, prodrug, or pharmaceutically acceptable salt thereof, and poly-D-L-lactide-co-glycolide (PLGA), wherein the microparticle has an average diameter of from about 50 μm to about 150 μm.

In certain embodiments, the methods and compositions described herein employ a "therapeutically effective" dose or dosing regimen of one or more Notch signaling inhibitor compounds, such as GSIs. The precise amount of a therapeutically effective dose or dosing regimen of the compounds will vary depending upon a variety of factors, including the activity of the specific compound or formulation employed; the metabolic stability and length of action of the compound or formulation; the age, body weight, general health, sex, and diet of the subject; the mode and time of administration; the rate of excretion; the drug combination, if employed; the severity of the particular disorder or condition; and the subject undergoing therapy.

In some instances, a therapeutically effective dose of one or more compounds is (e.g., for a 70 kg mammal) ranges from about 1.0 mg/kg (i.e., ~70 mg) to about 2500 mg/kg (i.e., ~175 g). In some embodiments, a therapeutically effective dose is administered at least once on a daily, weekly, bi-weekly, or monthly basis, or is administered at least twice or 3, 4, 5 or more times on a daily, weekly, bi-weekly, or monthly basis.

In certain embodiments, the methods or compositions described herein increase expression of UCP-1, for example, in white adipose tissue. In some instances, UCP-1 expression is increased by about or at least about 2, 5, 10, 50, 100, 500, or 1000-fold relative to a baseline reference or control. In certain embodiments, the methods or compositions described herein increase browning of white adipose tissue in the subject, for example, by about or at least about 5, 10, 20, 30, 40, 50, 60, 70, 80, 90, or 100%, relative to a baseline reference or control. In certain embodiments, the methods or compositions described herein reduce white adipose tissue in the subject, for example, by about or at least about 5, 10, 20, 30, 40, or 50% or more, relative to a baseline reference or control.

In certain embodiments, the methods or compositions described herein reduce body weight and/or body mass index (BMI) in the subject, for example, by about or at least about 5, 10, 20, 30, 40, or 50% or more, relative to a baseline reference or control. In some embodiments, body weight is reduced by about or at least about 5, 10, 20, 30, 40, 50, 60, 70, 80, 90, or 100 kg or more, relative to a baseline reference or control. In certain embodiments, the methods or compositions described herein reduce BMI in the subject, for example, by about or at least about 1, 2, 3, 4, 5, 6, 7, 8, 9, 10, 11, 12, 13, 14, 15, 16, 17, 18, 19, or 20 $kg/m^2$. In particular embodiments, the reduced body weight and/or reduced BMI in the subject is maintained for about or at least about 1, 2, 3, 4, 5, 6, 7, 8, 9, or 10 years or more.

In certain embodiments, the methods or compositions described herein improve glucose homeostasis in the subject, including wherein the subject has, or is at risk for developing, prediabetes or T2DM. For instance, certain embodiments reduce levels of fasting glucose in the subject, for example, by about or at least about 10, 20, 30, 40, or 50% or more, relative to a baseline reference or control. Some embodiments reduce fasting glucose levels in the subject to about or less than about 100 mg/dL. Certain embodiments increase glucose tolerance in the subject, for example, by about or at least about 10, 20, 30, 40, or 50% or more, relative to a baseline reference or control. Certain embodiments increase glucose tolerance to a level of about or less than about 140 mg/dL, as measured in an oral glucose tolerance test. In some instances, a baseline reference or control includes a measurement or value obtained prior to initiation of treatment or at an earlier time point during a treatment regimen.

In certain embodiments, the methods or compositions described herein increase life expectancy in the subject, for instance, by about or at least about 1, 2, 3, 4, 5, 6, 7, 8, 9, 10, 11, 12, 13, 14, 15, 16, 17, 18, 19, or 20 years or more.

For in vivo use, as noted above, for the treatment of human disease, the one or more Notch signaling inhibitor compounds and other agents described herein are generally incorporated into one or more pharmaceutical or therapeutic compositions prior to administration.

Thus, certain embodiments relate to pharmaceutical or therapeutic compositions that comprise a therapeutically effective amount or dose of one or more Notch signaling inhibitor compounds, as described herein. In some instances, a pharmaceutical or therapeutic composition described herein comprises one or more Notch signaling inhibitor compounds in combination with a pharmaceutically or physiologically acceptable carrier or excipient. Certain pharmaceutical or therapeutic compositions further comprise at least one additional agent, as described herein.

Administration of a composition may be achieved by a variety of different routes, including parenteral and enteral administration. Examples of parenteral administration include subcutaneous, intravenous (by IV infusion), intrathecal, epidural, intracerebral, intracerebroventricular, intranasal, intramuscular, intra-arterial, and inhalational administration. Examples of enteral administration include oral or rectal administration. Specific embodiments include directly or site-specifically administering the composition or compound to a subject at a site, or proximal to a site, which contains white adipose tissue.

Illustrative means of parenteral administration include needle (including microneedle) injectors, needle-free injectors, and infusion techniques, as well as any other means of parenteral administration recognized in the art. Parenteral formulations are typically aqueous solutions which may contain excipients such as salts, carbohydrates and buffering agents (preferably at a pH in the range from about 3 to about 9), but, for some applications, they may be more suitably formulated as a sterile non-aqueous solution or as a dried form to be used in conjunction with a suitable vehicle such as sterile, pyrogen-free water. The preparation of parenteral formulations under sterile conditions, for example, by lyophilization, may readily be accomplished using standard pharmaceutical techniques well known to those skilled in the art. Parenteral administration of a compound is illustratively performed in the form of saline solutions or with the compound incorporated into liposomes. In cases where the compound in itself is not sufficiently soluble to be dissolved, a solubilizer such as ethanol can be applied.

In some embodiments, the pharmaceutical compositions described herein do not significantly form aggregates, have a desired solubility, and/or have an immunogenicity profile that is suitable for use in humans, as known in the art. Thus, in some embodiments, a composition comprising one or more Notch signaling inhibitor compounds has about or less than about 50, 45, 40, 35, 30, 25, 20, 15, 14, 13, 12, 11, 10, 9, 8, 7, 6, 5, 4, 3, 2, or 1% aggregates, as measured, for example, by dynamic light scattering. Some compositions comprise one or more Notch signaling inhibitor compounds (for example, a GSI) that are at least about 50%, about 60%, about 70%, about 80%, about 90% or about 95% monodisperse with respect to the apparent molecular mass of non-aggregated Notch signaling inhibitor compounds (for example, a GSI).

In certain embodiments, as noted above, a pharmaceutical composition comprises a Notch signaling inhibitor compound (for example, a GSI) and one or more additional agents, for example, an additional agent for treating obesity or a comorbidity thereof, or for a treating metabolic disease, as described herein. The combination therapies described herein may include administration of a single pharmaceutical dosage formulation, which comprises one or more Notch signaling inhibitor compounds and an additional agent, as well as administration of compositions comprising one or more Notch signaling inhibitor compounds and an additional agent each in its own separate pharmaceutical dosage formulation. For example, one or more Notch signaling inhibitor compounds and an additional agent can be administered to the subject together in a single dosage composition, or each agent administered in separate dosage formulations. For instance, the one or more Notch signaling inhibitor compounds and additional therapeutic agent can be administered to the subject together in a single parenteral dosage composition such as in a saline solution or other physiologically acceptable solution, or each agent administered in separate parenteral dosage formulations. Where separate dosage formulations are used, the compositions can be administered at essentially the same time (i.e., concurrently), or at separately staggered times (i.e., sequentially) and in any order. Combination therapy is understood to include all these regimens.

In some instances, to prepare a pharmaceutical or therapeutic composition, an effective or desired amount of one or more agents is mixed with any pharmaceutical carrier(s) or excipient known to those skilled in the art to be suitable for the particular agent and/or mode of administration. A pharmaceutical carrier may be liquid, semi-liquid or solid. Solutions or suspensions used for parenteral, intradermal, subcutaneous, or topical application may include, for example, a sterile diluent (such as water), saline solution (e.g., phosphate buffered saline; PBS), fixed oil, polyethylene glycol, glycerin, propylene glycol or other synthetic solvent; antimicrobial agents (such as benzyl alcohol and methyl parabens); antioxidants (such as ascorbic acid and sodium bisulfite) and chelating agents (such as ethylenediaminetetraacetic acid (EDTA)); buffers (such as acetates, citrates and phosphates). If administered intravenously (e.g., by IV infusion), examples of suitable carriers include physiological saline or phosphate buffered saline (PBS), and solutions containing thickening and solubilizing agents, such as glucose, polyethylene glycol, polypropylene glycol, and mixtures thereof.

Administration of agents described herein, in pure form or in an appropriate therapeutic or pharmaceutical composition, can be carried out via any of the accepted modes of administration of agents for serving similar utilities. The compositions can be prepared by combining an agent-containing composition with an appropriate physiologically acceptable carrier, diluent, or excipient, and may be formulated into preparations in solid, semi solid, liquid or gaseous forms, such as tablets, capsules, powders, granules, ointments, solutions, suppositories, injections, inhalants, gels, microspheres, and aerosols. In addition, other pharmaceutically active ingredients and/or suitable excipients such as salts, buffers and stabilizers may, but need not, be present within the composition.

Carriers can include, for example, pharmaceutically or physiologically acceptable carriers, excipients, or stabilizers that are non-toxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as polysorbate 20 (TWEEN™) polyethylene glycol (PEG), and poloxamers (PLURONICS™), and the like.

In some embodiments, one or more agents can be entrapped in microcapsules prepared, for example, by coacervation techniques or by interfacial polymerization (for example, hydroxymethylcellulose or gelatin-microcapsules and poly-(methylmethacylate)-microcapsules, respectively), in colloidal drug delivery systems (for example, liposomes, albumin microspheres, microemulsions, nanoparticles and nanocapsules), or in macroemulsions. Such techniques are disclosed in Remington's Pharmaceutical Sciences, 16th edition, Oslo, A., Ed., (1980). The particle(s) or liposomes may further comprise other therapeutic or diagnostic agents.

A therapeutic or pharmaceutical composition may be in the form of a solid or liquid. In one embodiment, the carrier(s) are particulate, so that the compositions are, for example, in tablet or powder form. The carrier(s) may be liquid, with the compositions being, for example, an oral oil, injectable liquid or an aerosol, which is useful in, for example, inhalatory administration. When intended for oral administration, the pharmaceutical composition is preferably in either solid or liquid form, where semi-solid, semi-liquid, suspension and gel forms are included within the forms considered herein as either solid or liquid. Certain embodiments include sterile, injectable solutions.

As a solid composition for oral administration, the pharmaceutical composition may be formulated into a powder, granule, compressed tablet, pill, capsule, chewing gum, wafer or the like. Such a solid composition will typically contain one or more inert diluents or edible carriers. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent. When the pharmaceutical composition is in the form of a capsule, for example, a gelatin capsule, it may contain, in addition to materials of the above type, a liquid carrier such as polyethylene glycol or oil.

The therapeutic or pharmaceutical composition may be in the form of a liquid, for example, an elixir, syrup, solution, emulsion, or suspension. The liquid may be for oral administration or for delivery by injection, as two examples. When intended for oral administration, preferred composition contain, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer, and/or isotonic agent may be included.

The liquid therapeutic or pharmaceutical compositions, whether they be solutions, suspensions, or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes, or multiple dose vials made of glass or plastic. Physiological saline is a preferred adjuvant. An injectable pharmaceutical composition is preferably sterile.

The therapeutic or pharmaceutical composition may include various materials, which modify the physical form of a solid or liquid dosage unit. For example, the composition may include materials that form a coating shell around the active ingredients. The materials that form the coating shell are typically inert, and may be selected from, for example, sugar, shellac, and other enteric coating agents. Alternatively, the active ingredients may be encased in a gelatin capsule. The therapeutic or pharmaceutical compositions in solid or liquid form may include a component that binds to agent and thereby assists in the delivery of the compound. Suitable components that may act in this capacity include monoclonal or polyclonal antibodies, one or more proteins or a liposome.

The therapeutic or pharmaceutical composition may consist essentially of dosage units that can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols may be delivered in single phase, bi-phasic, or tri-phasic systems in order to deliver the active ingredient(s). Delivery of the aerosol includes the necessary container, activators, valves, subcontainers, and the like, which together may form a kit. One of ordinary skill in the art, without undue experimentation may determine preferred aerosols.

The compositions described herein may be prepared with carriers that protect the agents against rapid elimination from the body, such as time release formulations or coatings. Such carriers include controlled release formulations, such as, but not limited to, implants and microencapsulated delivery systems, and biodegradable, biocompatible polymers, such as ethylene vinyl acetate, polyanhydrides, polyglycolic acid, polyorthoesters, polylactic acid and others known to those of ordinary skill in the art.

The therapeutic or pharmaceutical compositions may be prepared by methodology well known in the pharmaceutical art. For example, a therapeutic or pharmaceutical composition intended to be administered by injection may comprise one or more of salts, buffers and/or stabilizers, with sterile, distilled water so as to form a solution. A surfactant may be added to facilitate the formation of a homogeneous solution or suspension. Surfactants are compounds that non-covalently interact with the agent so as to facilitate dissolution or homogeneous suspension of the agent in the aqueous delivery system.

The precise dosage and duration of treatment is a function of the disease being treated and may be determined empirically using known testing protocols or by testing the compositions in model systems known in the art and extrapolating therefrom. Controlled clinical trials may also be performed. Dosages may also vary with the severity of the condition to be alleviated. A pharmaceutical composition is generally formulated and administered to exert a therapeutically useful effect while minimizing undesirable side effects. The composition may be administered one time, or may be divided into a number of smaller doses to be administered at intervals of time. For any particular subject, specific dosage regimens may be adjusted over time according to the individual need.

Therapeutic or pharmaceutical compositions according to certain embodiments of the present disclosure are formulated so as to allow the active ingredients contained therein to be bioavailable upon administration of the composition to a subject or patient. Compositions that will be administered to a subject or patient may take the form of one or more dosage units. Actual methods of preparing such dosage forms are known, or will be apparent, to those skilled in this art; for example, see *Remington: The Science and Practice of Pharmacy,* 20th Edition (Philadelphia College of Pharmacy and Science, 2000). The composition to be administered will typically contain a therapeutically effective amount of an agent described herein, for treatment of a disease or condition of interest.

Also included are patient care kits, comprising (a) a therapeutically effective dose of one or more Notch signaling inhibitor compounds (for example, a GSI), as described herein; and optionally (b) at least one additional agent. In certain kits, (a) and (b) are in separate pharmaceutical or therapeutic compositions. In some kits, (a) and (b) are in the same pharmaceutical or therapeutic composition.

The kits herein may also include a one or more additional agents or other components suitable or desired for the indication being treated, or for the desired diagnostic application. The kits herein can also include one or more syringes or other components necessary or desired to facilitate an intended mode of delivery (e.g., stents, implantable depots, etc.).

In some embodiments, a patient care kit contains separate containers, dividers, or compartments for the composition(s) and informational material(s). For example, the composition(s) can be contained in a bottle, vial, or syringe, and the informational material(s) can be contained in association with the container. In some embodiments, the separate elements of the kit are contained within a single, undivided container. For example, the composition is contained in a bottle, vial, or syringe that has attached thereto the informational material in the form of a label. In some embodiments, the kit includes a plurality (e.g., a pack) of individual containers, each containing one or more unit dosage forms (e.g., a dosage form described herein) of one or more Notch signaling inhibitor compounds (for example, a GSI) and optionally at least one additional agent. For example, the kit includes a plurality of syringes, ampules, foil packets, or blister packs, each containing a single unit dose of the one or more Notch signaling inhibitor compounds (for example, a GSI) and optionally at least one additional agent. The containers of the kits can be air tight, waterproof (e.g., impermeable to changes in moisture or evaporation), and/or light-tight.

The patient care kit optionally includes a device suitable for administration of the composition, e.g., a syringe, inhalant, dropper, swab, or any such delivery device. Also included are methods of providing a kit, e.g., by combining the components described herein.

EXAMPLES

Example 1: Effects of Notch Signaling Inhibitors on Adipocytes

Experiments were performed to evaluate the role of Notch signaling an adipogenesis. The process of adipogenesis includes five steps, which are cell proliferation, cell contact inhibition/growth arrest, clonal expansion, permanent growth arrest, and lipid accumulation [10]. The transcriptional control of adipogenesis involves the activation of several families of transcription factors, such as CCAAT/enhancer binding protein family proteins (C/EBPs) and peroxisomal proliferator-activated receptor family proteins (PPARs). Adipogenic stimuli induce the increased expression of PPARγ and C/EBPα. Subsequently, C/EBPα directly binds to PPARγ promoter and results in its expression. Previous studies have shown that Notch signaling is involved in adipogenesis, however, paradoxical results were observed with Notch signaling either promoting or inhibiting the differentiation of 3T3-L1 preadipocytes [7][11]. In human primary cell cultures, inhibition of Notch signaling has been shown to facilitate adipogenic differentiation of adipose-derived mesenchymal stem cells [12].

Previous studies on the role of Notch signaling in adipogenesis have principally focused on white adipocyte differentiation with few studies reporting how Notch signaling regulates beige adipogenesis and mitochondrial biogenesis [15][16]. Herein, γ-secretase inhibitors (GSIs) were tested in an in vitro culture of 3T3-L1 preadipocytes for their ability to inhibit Notch signaling, and promote adipocyte browning and mitochondrial biogenesis. These findings provide insights into the contribution of Notch inhibition in the metabolism of adipose tissue, highlight the potential of cross-therapeutic application of GSIs to obesity or metabolic disorder treatment via inhibition of γ-secretase mediated processing of Notch signaling, and bridge the gap between basic science and clinical investigation.

Materials. MK-0752 was purchased from APExBIO (Houston, TX, USA). RO4929097, PF-03084014, LY3039478, and LY450139 were obtained from Sellechchem (Houston, TX, USA). BMS-708163 and BMS-906024 were purchased from Tocris Bioscience (Bristol, UK) and MilliporeSigma (Burlington, MA, USA), respectively. CellTiter 96® $AQ_{ueous}$ one solution reagent containing a tetrazolium compound [344,5-dimethylthiazol-2-yl)-5-(3-carboxymethoxyphenyl)-2-(4-sulfophenyl)-2H-tetrazolium, inner salt; MTS] was purchased from Promega (Madison, WI, USA). UCP1 antibody (ab10983) and goat polyclonal secondary antibody to rabbit immunoglobulin G (IgG)-H&L (Alexa Fluor® 488, ab150077) were obtained from Abcam (Cambridge, UK). CCAAT/enhancer-binding protein alpha (C/EBPα, SC-61), and β-Actin (SC-47778)

antibodies were purchased from Santa Cruz Biotechnology (Dallas, TX, USA). Peroxisome proliferator-activated receptor gamma (PPARγ, 81B8) and horseradish peroxidase (HRP)-conjugated secondary antibodies, including anti-rabbit IgG (7074S) and anti-mouse IgG (7076S), were purchased from Cell Signaling Technology (Danvers, MA, USA). All other reagents and solvents were purchased from Sigma-Aldrich (St. Louis, MO, USA).

Cell culture and drug treatment. 3T3-L1 preadipocytes were cultured in Dulbecco's modified Eagle medium (DMEM) supplemented with 10% fetal bovine serum (FBS) and 1% antibiotics (penicillin and streptomycin) at 37° C., 5% $CO_2$, and 95% relative humidity. The medium was routinely changed every two days and cells were separated by trypsin before reaching confluency. Beige adipocyte differentiation was induced by treating confluent preadipocytes with the adipogenic induction medium containing DMEM, 10% FBS, 0.5 mM isobutylmethylxanthine, 1 μM dexamethasone, 1.75 μM insulin, and 1 μM rosiglitazone. Three days after induction, medium was switched to the differentiation medium containing DMEM, 10% FBS, 850 nM insulin, and 10 nM triiodothyronine until adipocytes matured. For the drug treatment, a series of GSIs were added to the cells in culture medium at the same final drug concentrations of 0.5, 1, and 10 μM, respectively, and cells were induced for differentiation.

Assessment of cell viability. In vitro cell viability after incubation with various GSIs at three concentrations was determined using an MTS assay, which is based on the mitochondrial conversion of a tetrazolium salt. 3T3-L1 preadipocytes were seeded onto 96-well plates at a density of $1\times10^4$ cells per well and cultured in 5% CO2 at 37° C. for 48 h. GSIs were then added to the cells in culture medium at the same final drug concentrations of 0.5, 1, and 10 μM, respectively, and cells were further incubated at 37° C. for 12 h. Subsequently, 20 μL of CellTiter 96® $AQ_{ueous}$ one solution reagent was added to each well in 100 μL of culture medium and incubated at 37° C. in a humidified, 5% $CO_2$ atmosphere for 2 h. The absorbance was measured using a Tecan Spark™ 10M microplate reader (Tecan, Mannedorf, Switzerland) at a wavelength of 490 nm with background subtraction at 680 nm. Cells incubated with 0.1% Triton X-100 and dimethyl sulfoxide (DMSO) in culture medium served as positive and negative controls, respectively.

Morphological observations. The morphology of mature adipocytes after treatments with various GSIs was observed using a Leica DM 6000B microscope (Leica Camera, Wetzlar, Germany) with a ×20 objective. Oil Red O staining was subsequently conducted to demonstrate the presence of accumulated lipid droplets in the cells. Briefly, cells were fixed with 4% paraformaldehyde (PFA) and stained with freshly prepared Oil Red O working solutions containing 6 mL of Oil Red O stock stain (5 mg/mL in isopropanol) and 4 mL of $ddH_2O$ for 15 min. The stained cells were washed repeatedly with PBS and photographed using a Nikon D90 digital camera installed on a Leica DM 6000B microscope with a ×20 objective. After imaging, Oil Red O was extracted from stained cells using isopropanol and absorbance was determined spectrophotometrically at a wavelength of 500 nm.

RNA extraction, cDNA synthesis, and real-time qPCR. Total RNA was extracted from cells using TRIzol (Thermo Fisher Scientific, Waltham, MA, USA) in accordance with the manufacturer's protocol. RNA was treated with RNase-free DNase I to remove contaminating genomic DNA and the purity as well as concentration of extracted RNA were determined by a spectrophotometer NanoDrop 2000c (Thermo Fisher Scientific, Waltham, MA, USA). Subsequently, 2 μg of RNA was reverse transcribed to cDNA using random hexamer primers with M-MLV reverse transcriptase (Invitrogen, Carlsbad, CA, USA). Real-time qPCR was performed in the Roche Light Cycler 480 PCR system (Roche, Basel, Switzerland) with SYBR Green master mix. The sequences of gene-specific primers are listed in Table 2 below.

TABLE 2

Primer Sequences

| Gene | Sequence | SEQ ID NO: |
|---|---|---|
| Hes1 | 5'-GCACAGAAAGTCATCAAAGCC-3' | 1 |
| | 5'-TTGATCTGGGTCATGCAGTTG-3' | 2 |
| Fabp4 | 5'-GATGCCTTTGTGGGAACCT-3' | 3 |
| | 5'-CTGTCGTCTGCGGTGATTT-3' | 4 |
| Ppargc1α | 5'-AGCCGTGACCACTGACAACGAG-3' | 5 |
| | 5'-GCTGCATGGTTCTGAGTGCTAAG-3' | 6 |
| Cox5B | 5'-TTCAAGGTTACTTCGCGGAGT-3' | 7 |
| | 5'-CGGGACTAGATTAGGGTCTTCC-3' | 8 |
| Tmem26 | 5'-GAAACCAGTATTGCAGCACCC-3' | 9 |
| | 5'-CCAGACCGGTTCACATACCA-3' | 10 |
| Ucp1 | 5'-AGGCTTCCAGTACCATTAGGT-3' | 11 |
| | 5'-CTGAGTGAGGCAAAGCTGATTT-3' | 12 |
| Cidea | 5'-TGACATTCATGGGATTGCAGAC-3' | 13 |
| | 5'-GGCCAGTTGTGATGACTAAGAC-3' | 14 |
| Prdm16 | 5'-CAGCACGGTGAAGCCATTC-3' | 15 |
| | 5'-GCGTGCATCCGCTTGTG-3' | 16 |
| Dio2 | 5'-AATTATGCCTCGGAGAAGACCG-3' | 17 |
| | 5'-GGCAGTTGCCTAGTGAAAGGT-3' | 18 |

The $2^{-\Delta\Delta CT}$ method was used to analyze the relative changes of gene expression after normalization to the expression of β-Actin.

Protein extraction and western blotting. Total protein was extracted from cells using RIPA buffer containing 25 mM Tris-HCl (pH 8.0), 150 mM NaCl, 1 mM EDTA, 0.5% NP-40, 0.5% sodium deoxycholate and 0.1% SDS. Protein concentrations were determined by Pierce BCA Protein Assay Reagent (Pierce Biotechnology, Waltham, MA, USA). Proteins were separated by SDS-PAGE and transferred to a polyvinylidene fluoride membrane (Millipore, Burlington, MA, USA). The membrane was then blocked with 5% fat-free milk for 1 h at room temperature and incubated with primary antibodies in 5% milk overnight at 4° C. as well as secondary antibodies for 1 h at room temperature. Primary antibodies, including UCP1 (1:1000 dilution), C/EBPα (1:500 dilution), PPARγ (1:500 dilution), and β-Actin (1:5000 dilution), were used. HRP-conjugated secondary antibodies, including anti-rabbit and anti-mouse IgG, were also used at a dilution of 1:10,000. A luminol reagent for enhanced chemiluminescence detection of western blots (Santa Cruz Biotechnology, Dallas, TX, USA) was employed and signals were detected with a FluorChem R imaging system (ProteinSimple, San Jose, CA, USA).

Immunofluorescence staining. After washing with phosphate-buffered saline (PBS), cells were fixed with 4% PFA, quenched with glycine (100 mM glycine and 0.1% sodium azide in PBS), and blocked with PBS containing 2% BSA, 5% goat serum, and 0.2% Triton X-100 for 1 h at room temperature. Subsequently, cells were incubated with the UCP1 antibody diluted at 1:500 in the same blocking buffer overnight at 4° C. and the Alexa Fluor® 488 conjugated goat anti-rabbit IgG (1:1000 dilution) for 1 h at room temperature. Nuclei were counterstained with 4',6-diamidino-2-phenylindole (DAPI, 1 μg/mL), which was premixed with the secondary antibody.

Statistical analysis. All studies were performed in triplicate and data points were expressed as mean values plus or minus standard error of the mean (mean±SEM). To determine statistical significance, analysis of variance (one-way or two-way ANOVA) followed by Tukey's multiple comparison test was performed using GraphPad Prism 7. Differences were considered statistically significant if $p \leq 0.05$.

Figure 1A:
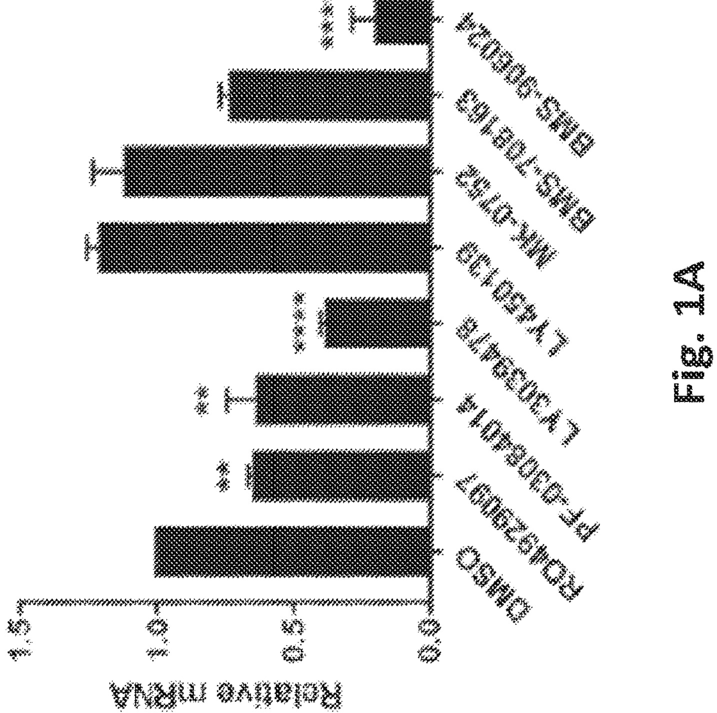

Effects of GSIs on Notch inhibition. To determine the impact of GSIs on inhibition of Notch signaling, 3T3-L1 preadipocytes were treated with a series of GSIs (see Table 1) at a concentration of 1 μM and the change in mRNA expression of Hes1, a Notch downstream transcriptional target gene, was evaluated using real-time qPCR. As shown in FIG. 1A, the expression of Hes1 was significantly inhibited after the treatment with RO4929097 ($p \leq 0.01$), PF-03084014 ($p \leq 0.01$), LY3039478 ($p \leq 0.001$), and BMS-906024 ($p \leq 0.001$), suggesting efficient inhibition of Notch signaling. However, other GSIs used in the experiment, including LY450139, MK-0752, and BMS-708163, did not significantly decrease the expression level of Hes1 at the concentration of 1 μM (FIG. 1A). The difference in inhibitory activity of Notch signaling among drug treatments might be due to variable effective concentrations.

To further examine the relationship between drug concentration and inhibitory effect of GSIs, cells were treated with the four most promising inhibitors (i.e., RO4929097, PF-03084014, LY3039478, and BMS-906024) at three gradient concentrations (0.5, 1, and 10 μM). It was observed that the mRNA level of Hes1 was significantly downregulated by 40-50% across all the treatment groups compared to the DMSO control group (p 0.01), even at the lowest concentration of 0.5 μM (FIG. 1B). The inhibitory effect became more significant with increasing the drug concentration of PF-03084014, LY3039478, and BMS-906024, whereas the treatment of RO4929097 did not result in a dose-dependent depression in Hes1 expression. These results suggest that 3T3-L1 preadipocytes respond to a variety of GSIs with different sensitivity.

Figure 2:
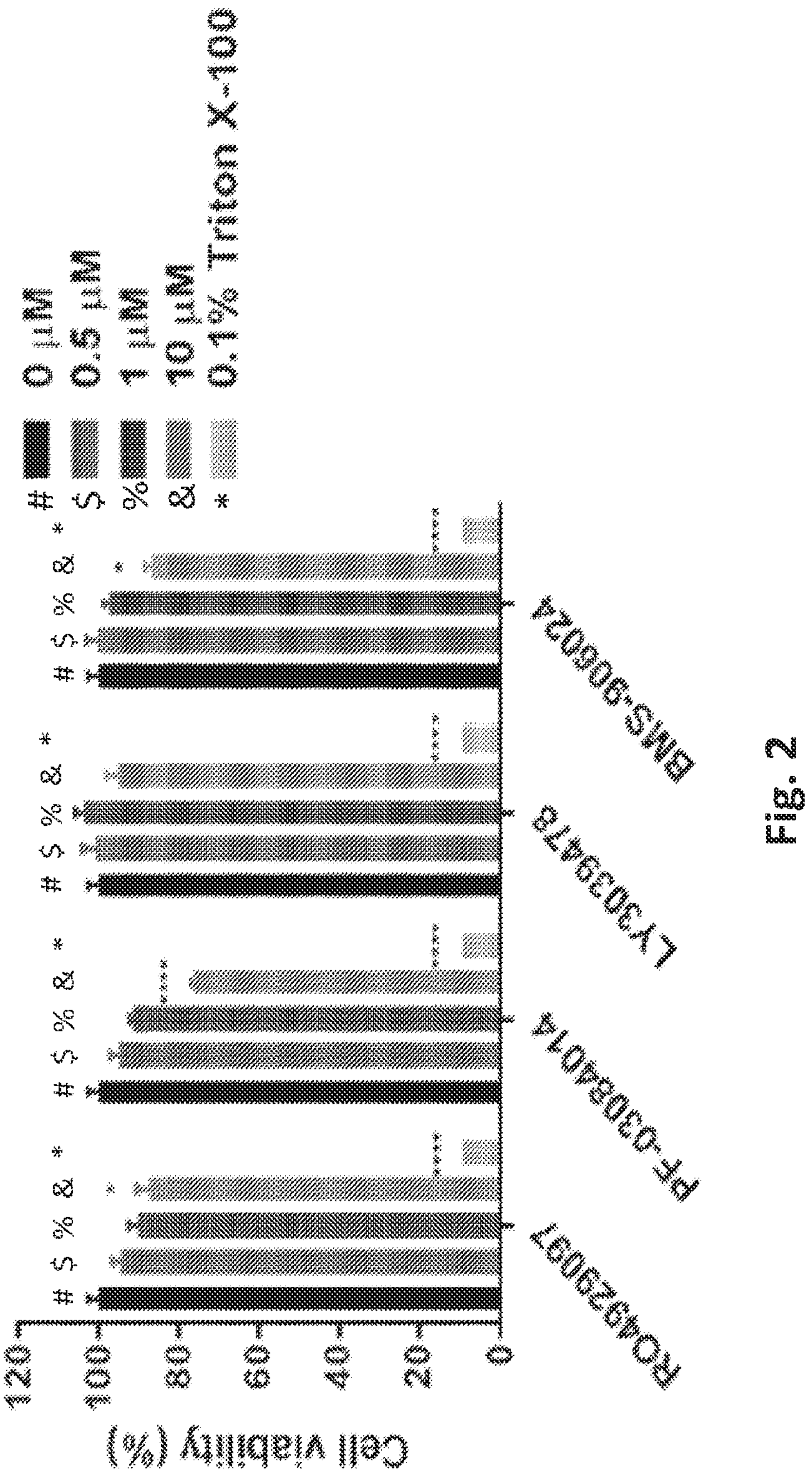
FIG. 2 shows the effects of GSIs on cell viability. 3T3-L1 preadipocytes were treated with four GSIs at concentrations of 0.5, 1, and 10 μM. A DMSO vehicle control without any inhibitors (0 μM) and a positive control of 0.1% Triton X-100 were also included. *$p<0.05$, $p<0.01$, *$p<0.005$ and ****$p<0.001$ (Two-way ANOVA followed by Tukey's multiple comparison test). Data are shown as mean±SEM. n=3 individual experiments.

Effects of GSIs on cell viability. To investigate effects of GSIs on cell viability, 3T3-L1 preadipocytes were treated with GSIs at three gradient concentrations (0.5, 1, and 10 μM) for 12 h. It was found that the cell viability after the treatment with RO4929097, PF-03084014, and BMS-906024 decreased with increasing the drug concentration from 0.5 to 10 μM (FIG. 2). Induction of cytotoxicity by these three GSIs was dose-dependent with most significant effects observed at the highest concentration of 10 μM, particularly in the group treated with PF-03084014 (p 0.001). The result is consistent with previously published data, showing inhibition of cell growth by PF-03084014 might be partially due to its effect on induction of cell cycle block and apoptosis [17]. LY3039478 did not result in any significant cytotoxicity at all the concentrations used, indicating the promising safety of this compound.

Figure 3B:
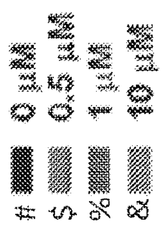
FIGS. 3A-3B show that GSIs promote differentiation efficiency of 3T3-L1 preadipocytes. 3T3-L1 preadipocytes were treated with four GSIs at concentrations of 0.5, 1, and 10 μM and induced for differentiation. A DMSO vehicle control without any inhibitors (0 μM) was also included. Medium containing GSIs were routinely changed every two days during differentiation.
Figure 3B:
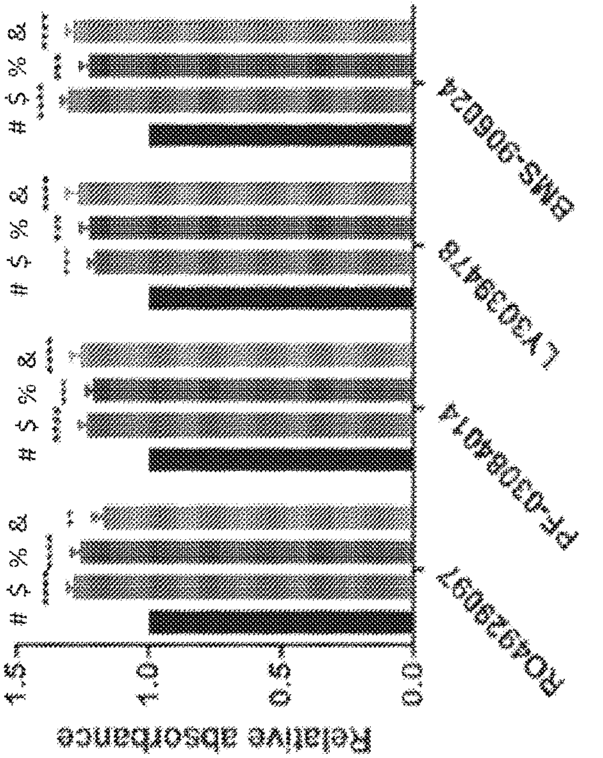
Figure 3A:
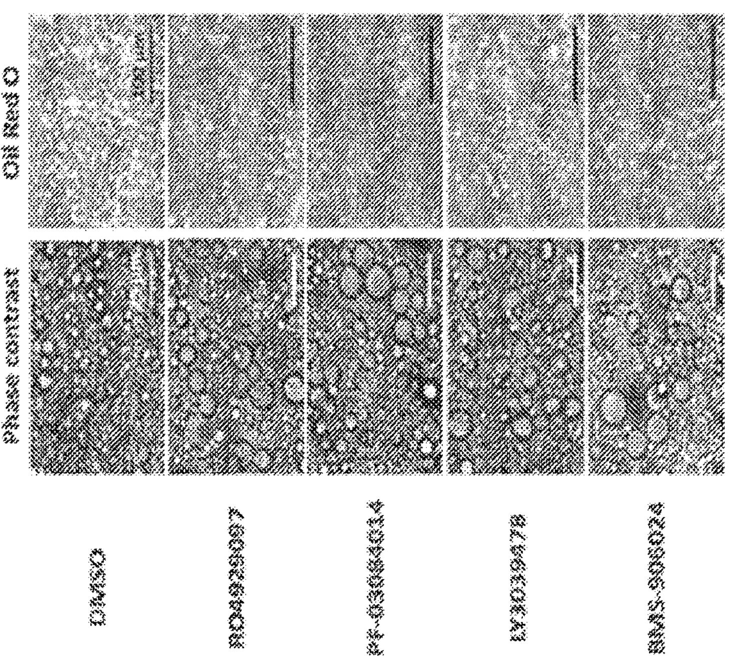

GSIs promote differentiation efficiency of 3T3-L1 preadipocytes. To determine the role of Notch signaling in adipogenesis, 3T3-L1 preadipocytes were treated with various GSIs at three gradient concentrations (0.5, 1, and 10 μM) after induced to differentiate. As shown in FIG. 3A, differentiation of 3T3-L1 cells was efficiently induced with lipid droplets accumulated in the cytoplasm after incubation with induction medium for three days followed by differentiation medium for five days. Both phase contrast and Oil Red 0 staining images confirmed that the number and size of lipid droplets increased in the GSI (1 μM) treated cells compared to the DMSO control, suggesting that GSIs enhanced the differentiation efficiency of 3T3-L1 cells. However, no obvious differences were observed among the four compounds. It was also noted that three gradient concentrations did not cause remarkable differences in the number and size of lipid droplets (Figure S1). Total lipid content within the cells was further determined by quantitative analysis of Oil Red 0 intensity. Results show that the absorbance value of Oil Red 0 extracted from the GSI treated cells was significantly higher than that in the control group (FIG. 3B), demonstrating that even very low dosages of GSIs promote the differentiation of 3T3-L1 cells and accumulation of lipid droplets.

Figure 4A:
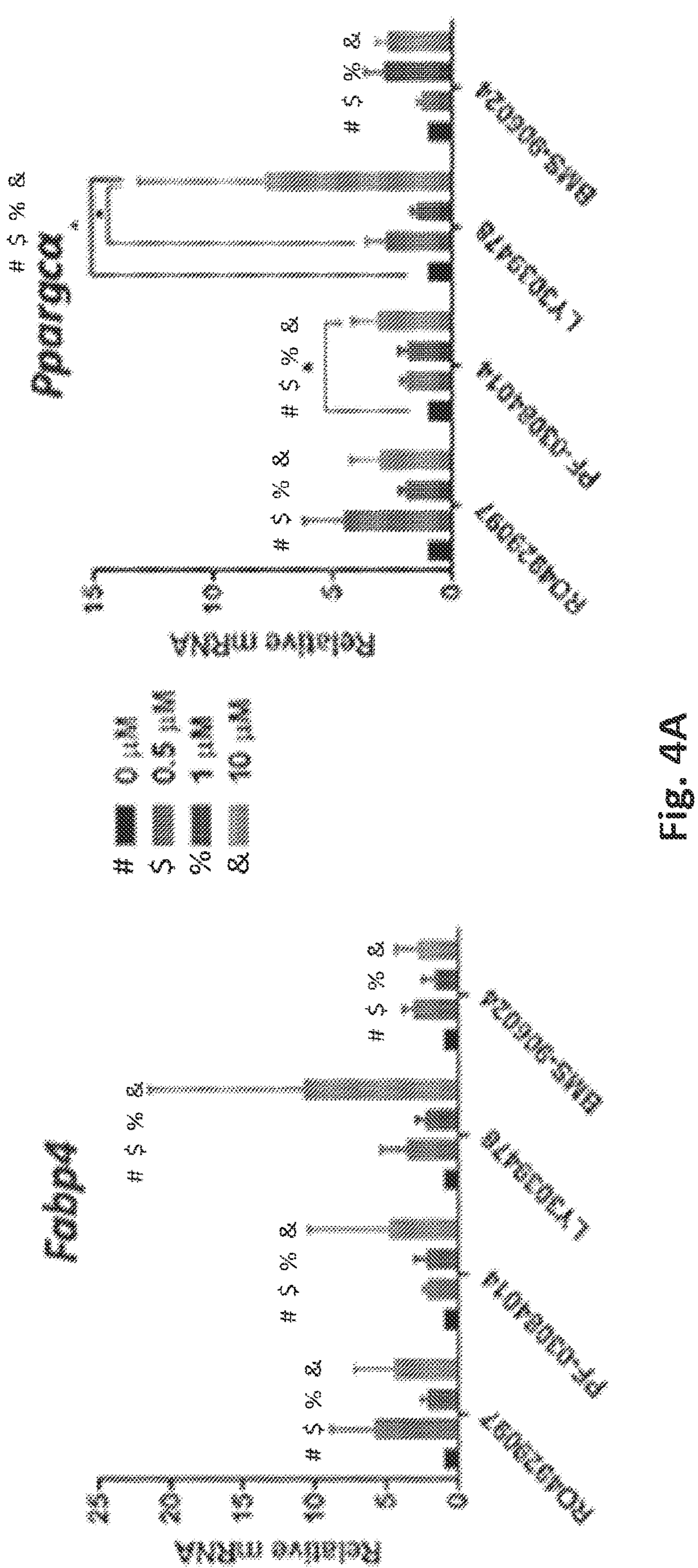
Figure 4B:
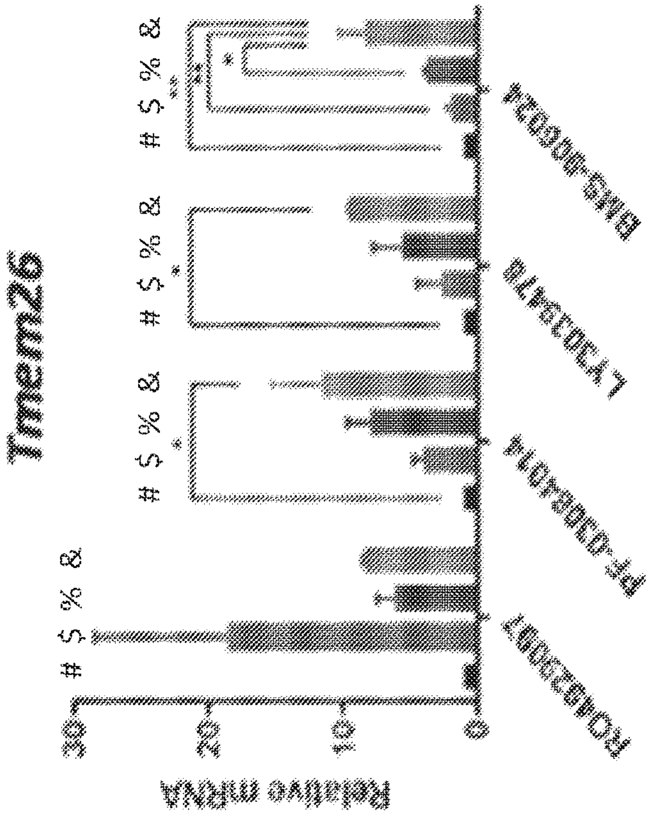
Figure 4B:
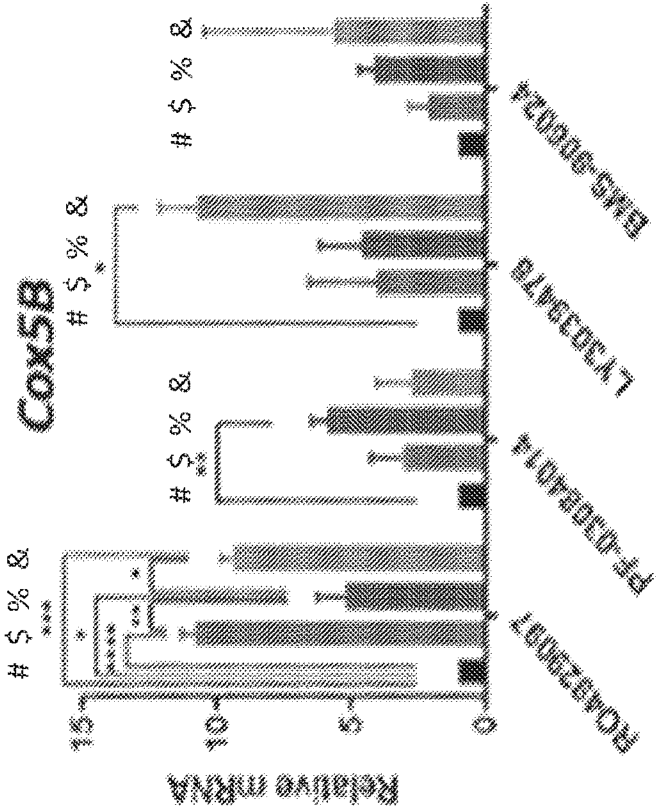

GSIs upregulate the expression of beige adipogenic and browning marker genes in differentiated 3T3-L1 cells. Although the Notch signaling has been shown to affect adipocyte differentiation, its potential role in regulation of beige adipocyte biogenesis has only been investigated recently [15]. To identify the impact of GSIs on beige adipogenesis, we examined the mRNA expression of adipogenic, mitochondria-related, and beige fat-selective genes in differentiated 3T3-L1 cells following the consecutive treatment with GSIs using real-time qPCR. As shown in FIG. 4A, the expression of fatty acid binding protein 4 (Fabp4) increased in the cells treated with GSIs at all the concentrations; however, the differences were not significant. The GSI treatments also upregulated the expression of peroxisome proliferator-activated receptor gamma coactivator 1-alpha (Ppargc1α) with significant changes observed in the groups treated with PF-03084014 and LY3039478 at the highest concentration of 10 μM ($p \leq 0.05$). In addition, FIG. 4B shows that RO4929097 increased the expression of cytochrome c oxidase subunit 5B (Cox5B) at all the concentrations with the low dose treatment inducing the most significant change ($p \leq 0.001$). Significant upregulation of Cox5B was also observed when cells were treated with 1 μM of PF-03084014 ($p \leq 0.01$) and 10 μM of LY3039478 ($p \leq 0.05$). PF-03084014, LY3039478, and BMS-906024 increased the expression of transmembrane protein 26 (Tmem26) in a dose-dependent manner with the highest dose causing significant differences between treatment and control groups. Furthermore, the expression of beige fat-selective genes, including uncoupling protein 1 (Ucp1), cell death-inducing DNA fragmentation factor alpha-like effector A (Cidea), PR domain containing 16 (Prdm16), and type 2 deiodinase (Dio2), was upregulated after the treatment with all the GSIs (FIG. 4C). However, significant changes were found only in the groups of PF-03084014 and LY3039478 with the high concentration of 10 μM (p 0.05). These results indicate that GSIs promote beige adipogenesis and mitochondrial biogenesis in differentiated adipocytes, but the optimal concentrations to achieve the maximum efficiency are variable for each compound.

Figure 4D:
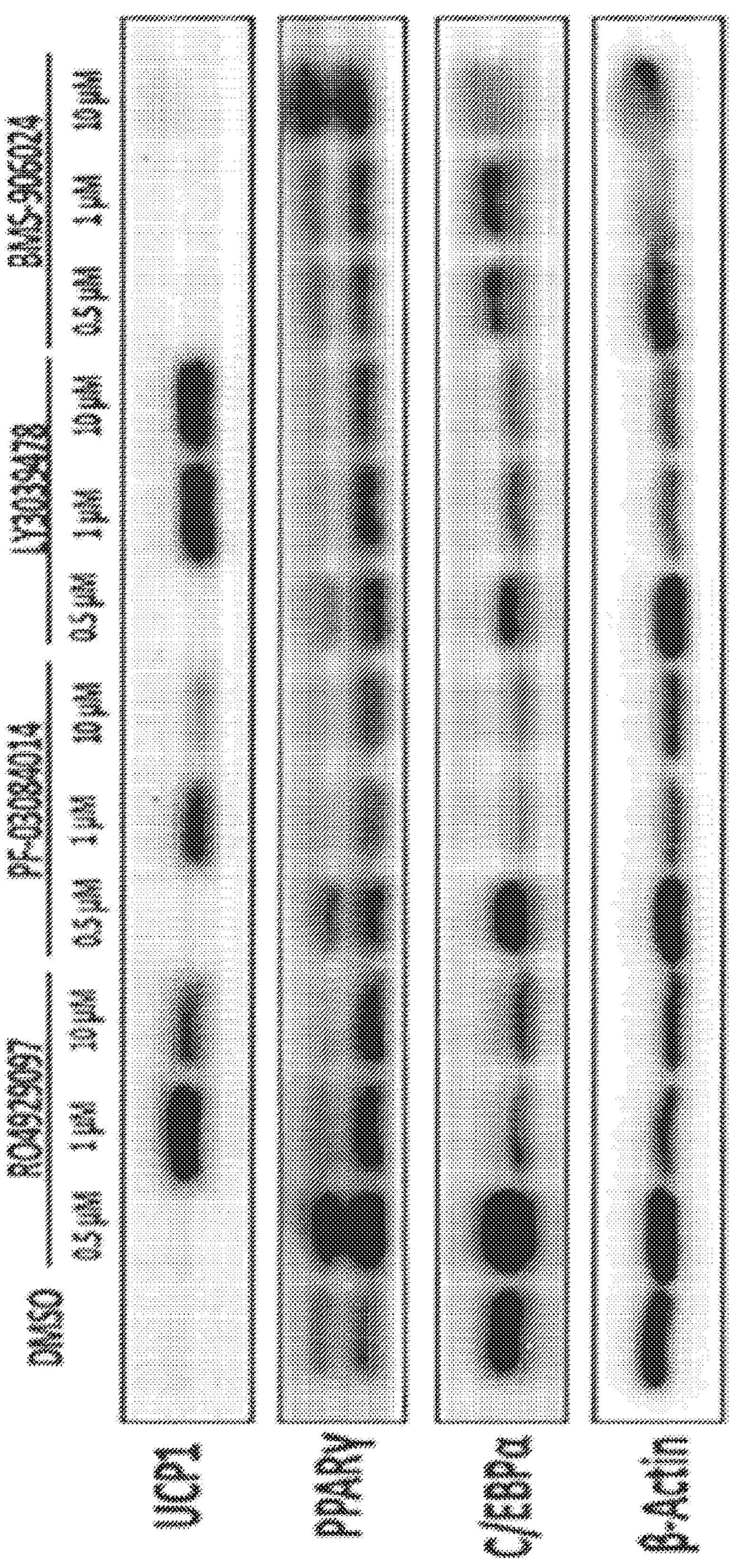
Figure 4E:
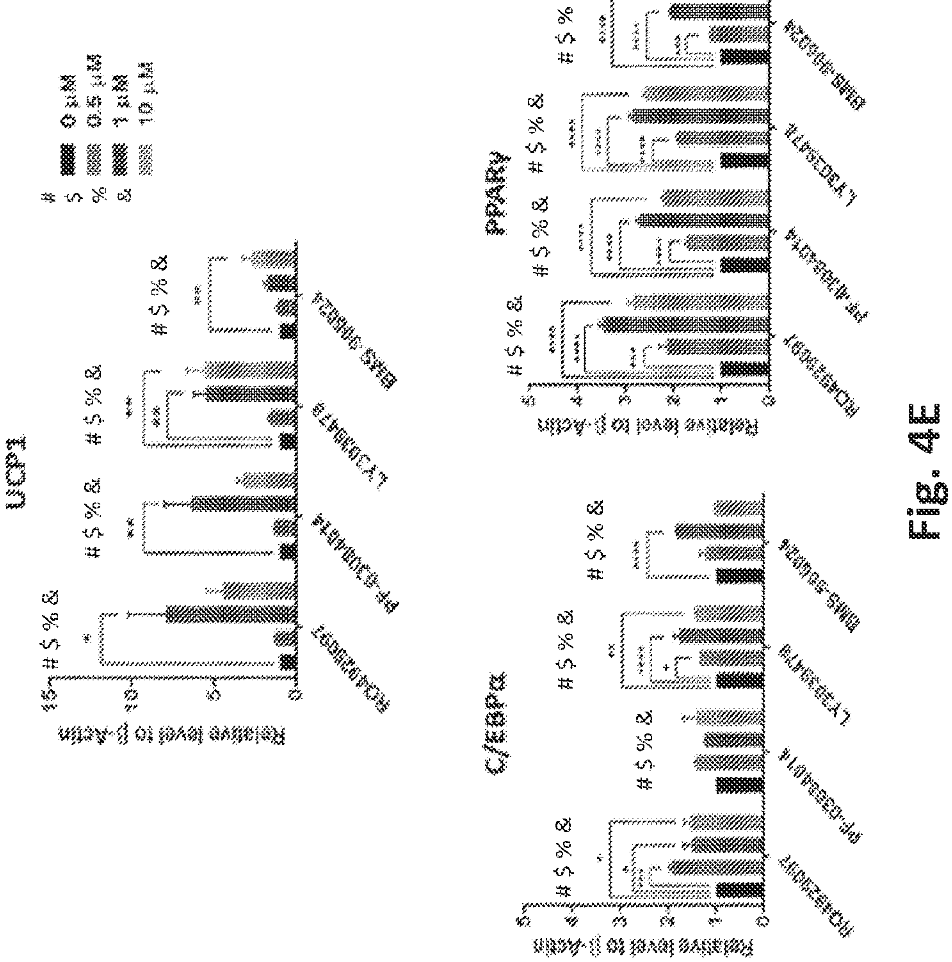

Western blot analysis revealed that the protein expression of UCP1 was significantly upregulated when cells were treated with 1 μM of RO4929097 (p 0.05) and PF-03084014 (p 0.01) (FIGS. 4D and 4E). However, the enhancement in expression level decreased by approximately 50% when increasing the concentration of GSIs from 1 to 10 μM, which might attribute to the cytotoxicity induced by the high dose. The protein expression of adipogenic markers, such as PPARγ and C/EBPα, was also evaluated. It was found that four GSIs significantly increased the expression level of PPARγ at all the concentrations. The expression of C/EBPα was significantly upregulated after the treatment with RO4929097 and LY3039478 at all the concentrations as well as 1 μM of BMS-906024 ($p \leq 0.005$). These results suggest that Notch inhibition mediated by GSIs promote adipogenesis and browning of white adipocytes. It was also noted that the low concentration of 0.5 μM was sufficient to increase the protein expression of PPARγ, but a higher concentration of 1 μM was observed to induce significant upregulation of UCP1.

Figure 5:
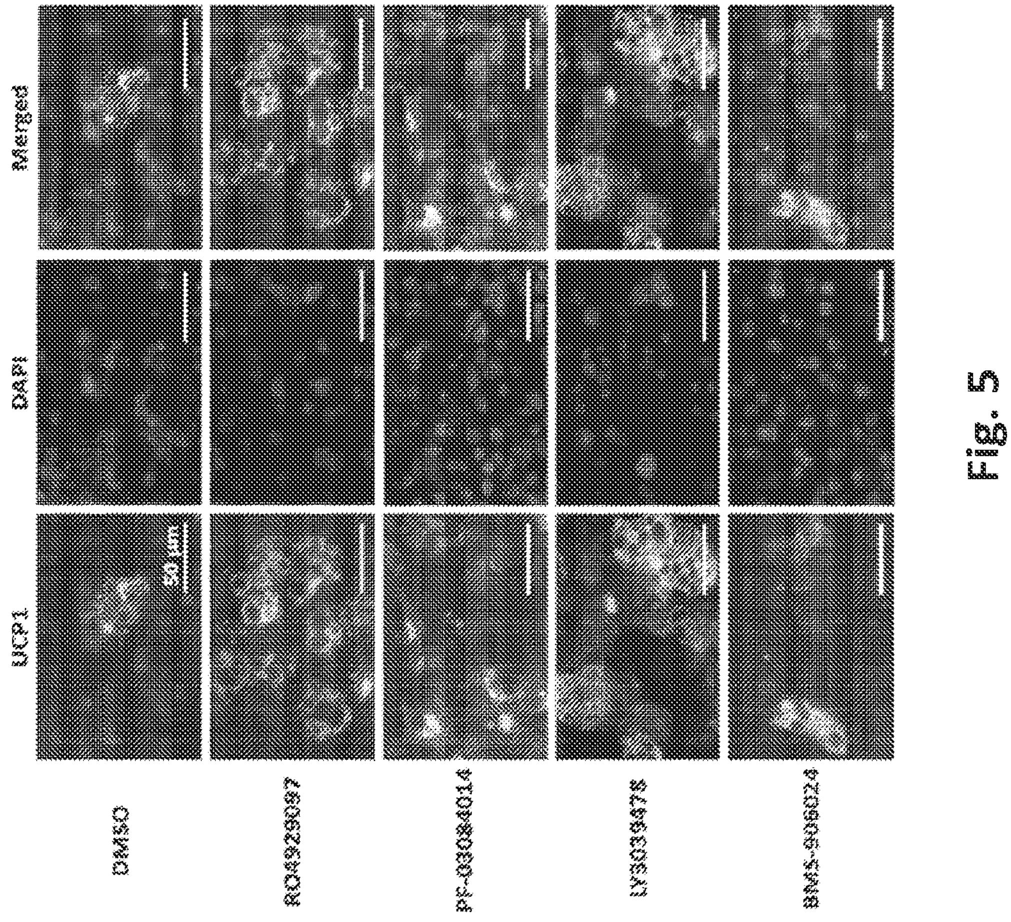
FIG. 5 shows that GSIs increase the protein expression of UCP1 in differentiated 3T3-L1 cells. 3T3-L1 preadipocytes were treated with four GSIs at the concentrations of 1 μM and induced for differentiation. A DMSO vehicle control without any inhibitors (0 μM) was also included. Medium containing GSIs were routinely changed every two days during differentiation. UCP1 was stained with Alexa Fluor® 488 in green and nuclei were counterstained with DAPI in blue.
Figure 6:
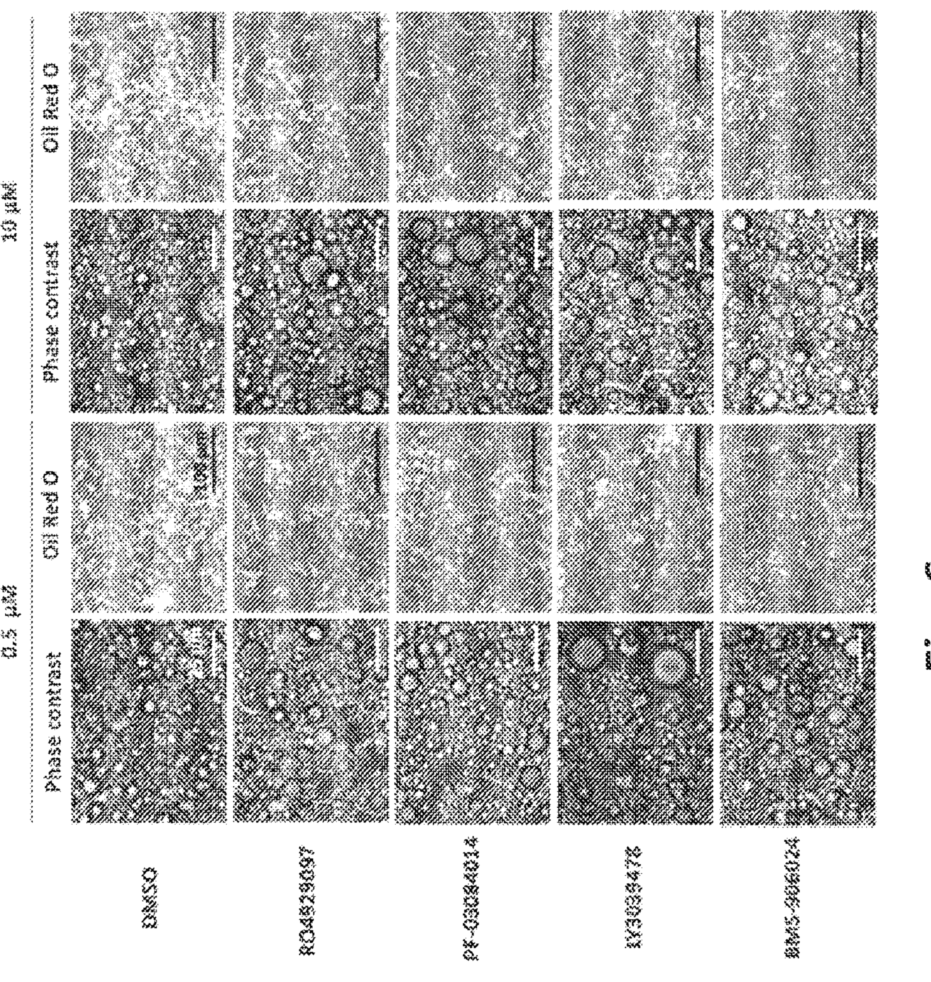
FIG. 6 shows that GSIs promote differentiation efficiency of 3T3-L1 preadipocytes, related to FIGS. 3A-3B. Phase contrast and bright field images of differentiated 3T3-L1 cells stained with Oil Red 0 after the treatment with GSIs. 3T3-L1 preadipocytes were treated with four GSIs at concentrations of 0.5 and 10 μM and induced for differentiation. A DMSO vehicle control without any inhibitors (0 μM) was also included. Medium containing GSIs were routinely changed every two days during differentiation.

GSIs promote the protein expression of UCP1 in differentiated 3T3-L1 cells. It has been shown that the increase in metabolic rate associated with induction of UCP1 is accompanied by enhanced mitochondrial biogenesis and fatty acid oxidation in WAT. To further confirm whether GSI enhances thermogenic activities of UCP1 at the cellular level, the expression of UCP1 in 3T3-L1 cells after the treatment with GSIs at the concentration of 1 μM was investigated by immunofluorescence staining. As shown in FIG. 5, the green fluorescence signal indicating UCP1 positive staining was detected in the cytoplasm of 3T3-L1 cells. Only few UCP1 positive adipocytes were observed in the control group treated with DMSO, whereas the number of positive adipocytes increased when the cells were treated with GSIs. Compared to RO4929097, PF-03084014, and LY3039478, BMS-906024 at the same concentration showed the minimal efficiency in increasing UCP1 expression, which is consistent with western blot results shown in FIGS. 4D and 4E. Taken together, the results demonstrate that GSIs could induce browning of white adipocytes by upregulating UCP1 expression.

Discussion

Notch signaling, an evolutionarily highly conserved pathway, is important in regulating cell-cell communication and cell-fate determination during normal development of most organs and tissues in the body. It has also been reported that Notch signaling is required in tissue homeostasis, such as hematopoietic system [18], vasculature [19], skeletal muscle [20], and adipose tissue [15]. Although understanding of signaling pathways that regulate adipogenesis has been considered a fundamental for the treatment of obesity with the role of Notch signaling characterized by various research groups [21][22], its function in modulating the adipocyte plasticity and beige adipocyte biogenesis has just been discovered recently [15]. Our studies have found that Notch signaling plays an important role in regulating adipocyte thermogenesis as well as conversion of white to beige adipocytes in mice, consequently affecting body energy metabolism [15]. It has been demonstrated that pharmacological inhibition of Notch signaling through administration of dibenzazepine promotes widespread browning of WAT. Specifically, the browning phenotype leads to metabolic beneficial effects, including enhanced energy expenditure, glucose tolerance, insulin sensitivity, and resistance to high fat diet-induced obesity. However, dibenzazepine is currently used for research only and its effects in humans have not been studied, challenging the translation of fundamental findings into clinical practice. Here, we screened a series of GSIs that have been found to be reasonably safe in phase 1 clinical trials and are currently being investigated in phase 2 or 3 for the treatment of cancer or Alzheimer's disease. Their impacts on inhibition of Notch signaling pathway and induction of browning of white adipocytes were systematically compared.

We found that four of seven GSIs, including RO4929097, PF-03084014, LY3039478, and BMS-906024, at the concentration of 1 μM significantly downregulated the mRNA expression of Notch downstream target gene Hes1 in the initial screening. The differences in inhibitory activity of Notch signaling induced by GSIs might be attributed to variable isoform-specific binding sites and mechanisms of action. In general, selective isoform inhibition is considered a relatively safe therapeutic strategy with reduced systemic toxicity, pan-inhibitors, on the other hand, could display enhanced inhibitory efficiency [23]. Indeed, our present results showed that isoform-specific inhibitors, such as BMS-708163 and MK-0752, exhibited relatively moderate inhibitory effect of Notch signaling compared to other pan-Notch inhibitors. Another possible factor that may contribute to the differences among these GSIs is the selectivity of blocking target. For instance, some compounds might not be specific for γ-secretase cleavage of Notch signaling with equally inhibiting the processing of many other γ-secretase substrates, such as β-amyloid. The comprehensive blocking effects could lead to distinct pharmacological consequences. The selected four compounds at three gradient concentrations were further investigated in the secondary screening with efficient inhibition of Notch achieved even at the lowest concentration of 0.5 μM. PF-03084014, LY3039478, and BMS-906024 exhibited a dose-dependent inhibition of Notch, whereas RO4929097 did not display a clear correlation between drug concentration and inhibitory activity in the range between 0.5 to 10 μM. This result suggests RO4929097 could be a very potent GSI targeting Notch signaling and the inhibitory activity might have reached its threshold at the concentration of 0.5 μM. Previously, in vitro inhibitory activity of Notch induced by RO4929097 has also been evaluated in human tumor-derived cells by Roche [24]. They found that the compound treatment led to a dose-dependent inhibition beginning at 0.1 μM, but no further reduction in protein and mRNA levels of Hes1 was observed when the concentration was higher than 0.5 and 1 μM, respectively.

We next determined the cytotoxicity of four GSIs at three concentrations in 3T3-L1 preadipocytes. We found that inhibiting γ-secretase activity by LY3039478 had no significant effect on cell viability at all the concentrations used. In contrast, cell viability decreased in a dose-dependent manner with the treatment with RO4929097, PF-03084014, and BMS-906024. The cytotoxic effect of GSIs might result from cell cycle arrest and consequent apoptotic cell death. Previous studies have shown that the treatment with GSIs could lead to a significant decrease in AKT phosphorylation and a constitutively active form of AKT block the inhibitor mediated cell cycle arrest and apoptotic cell death [25]. In addition, the question whether the cytotoxicity of GSIs is mediated by inhibition of proteasome activity or γ-secretase mediated processing of Notch signaling has also been a subject of several studies. For instance, Han et al. determined the cytotoxicity of GSI I in a number of cell lines, but the treatment with two highly specific GSI did not affect the survival of these cells [26]. The authors claimed that inhibition of proteasome activity was the major contributor to the observed cytotoxicity. Nevertheless, several questions regarding the action of GSIs in Notch signaling-independent mechanisms remain to be answered. Furthermore, in order to achieve enhanced intracellular transport of GSIs with minimized cytotoxicity, development of clinically translatable Notch-inhibiting drug delivery systems could be one of our future directions [16][27].

More importantly, we found that the treatment with GSIs promoted differentiation of 3T3-L1 preadipocytes and upregulated adipogenic marker genes at the level of transcription and translation. Our results are supported by previously reported data, showing that the Notch signaling is a negative regulator in adipogenesis of 3T3-L1 preadipocytes [28]. The process of adipogenesis involves downregulation of the gene encoding Hes1, which plays a dual role in adipocyte development as a suppresser and an activator. However, promoter analyses of up- and down-regulated genes in 3T3-L1 preadipocytes has demonstrated that the Notch signaling most likely inhibits adipogenesis through induction of Hes1 homodimers, which block the transcription of target genes. In addition, this effect could also be achieved by exposing 3T3-L1 preadipocytes to the Notch ligand Jagged1, associating with complete loss of PPARγ and C/EBPα [29]. This is supported by the findings in our study that GSIs, even at the lowest concentration of 0.5 μM are effective to induce the depressed transcription of Hes1 and the increased expression of adipogenic marker genes. Although PPARγ and C/EBPα are important regulators of the thermogenic program of beige adipocytes, additional transcriptional components that cooperate with them, particularly PRDM16 and PGCα have been shown to be necessary to activate the beige fat-selective gene program [30][31]. We therefore examined the expression of mitochondria-related and beige fat-selective genes. Results reveal that Notch inhibition induced by GSIs upregulate their expression levels, which is consistent with our previous findings that Notch target gene HES1 directly binds to the promoter regions of PRDM16 and PGCα to repress the transcription of these two master regulators of mitochondrial biogenesis and beige adipogenesis [15].

Furthermore, we determined the expression of UCP1, which has long been considered the key protein stimulating thermogenesis by uncoupling cellular respiration and mitochondrial ATP synthesis as well as playing a crucial role in regulation of adipose conversion [32][33]. In our study, significant upregulation of UCP1 was observed when cells were with RO4929097, PF-03084014, and LY3039478 at the concentration of 1 μM Compared to these three compounds, BMS-906024 had the minimal impact on the increase in UCP1 protein expression. Interestingly, the upregulated expression of UCP1 decreased by around 50% when a higher concentration of 10 μM was used in the groups treated with RO4929097 and PF-03084014. In contrast, the high concentration of LY3039478, has shown to be less cytotoxic than other compounds, did not significantly change the protein expression of UCP1. These results demonstrate that the efficiency of beige adipogenesis and browning of white adipocytes might be affected by the cytotoxicity induced by high-dose GSIs. Most studies to date use GSIs at a concentration of 10 μM to induce adipogenesis in vitro and investigate the role of Notch signaling [15][34]; however, our present findings confirm the efficiency of potent GSIs with relatively low concentrations and point out the importance of selecting the optimal dose that is sufficient to achieve pharmacological activity and would be expected to alleviate toxicities associated with overdose.

Conclusions

In the present study, we have shown that pharmacological inhibition of Notch signaling by clinical candidates of GSIs with an optimized concentration promotes beige adipogenesis and mitochondrial biogenesis in 3T3-L1 preadipocytes. These findings not only highlight the potential of cross-therapeutic application of GSIs to obesity and metabolic disease treatment via inhibition of γ-secretase mediated processing of Notch signaling, but also provide important experimental evidences to support further design and development of clinically translatable Notch-inhibiting drug delivery system.

Example 2: Characterization of PLGA Nanoparticles

Figure 7:
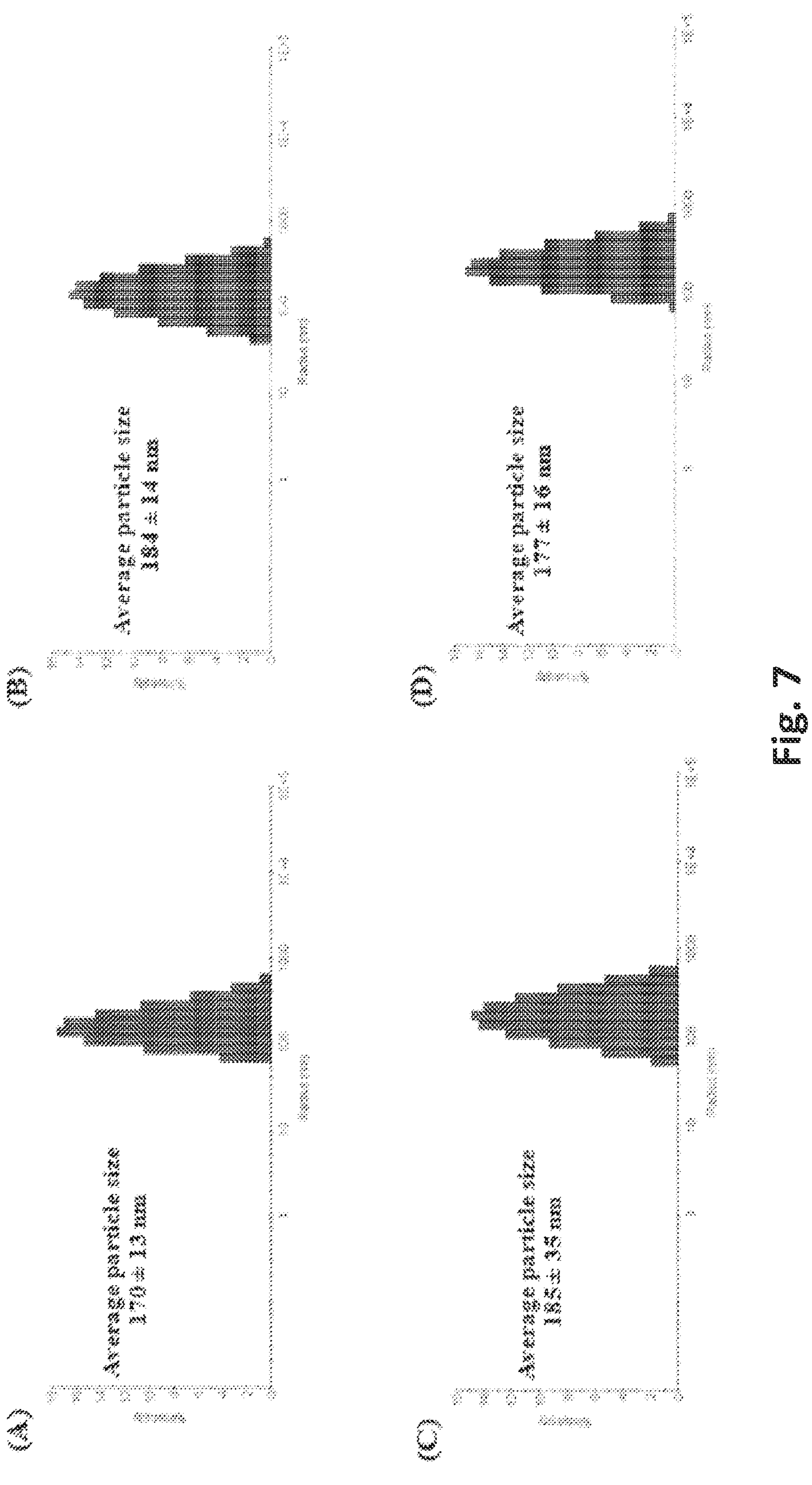
FIGS. 7A-7D is a series of graphs showing particle size distribution of various γ-secretase inhibitor-loaded PLGA NPs, measured using DynaPro PlateReader-II. The size distribution of (FIG. 7A) RO4929097-PLGA NPs.

Size distribution of various γ-secretase inhibitor-loaded PLGA NPs. The particle size distribution of various γ-secretase inhibitor-loaded PLGA NPs was measured. Formulated nanoparticulate (0.15 mg) re-suspended in 1 mL deionized water and the size distribution was measured using DynaPro PlateReader-II. The size distribution of (FIG. 7A) RO4929097-PLGA NPs; (FIG. 7B) PF-03084014-PLGA NPs; (FIG. 7C) LY3039478-PLGA NPs; and (FIG. 7D) BMS-906024-PLGA NPs is shown in Table 3.

TABLE 3

Size distribution of various γ-secretase inhibitor-loaded PLGA NPs

| Nanoparticle | Average Particle Size (nm) |
|---|---|
| RO4929097-PLGA | 170 ± 13 |
| PF-03084014-PLGA | 184 ± 14 |
| LY3039478-PLGA | 185 ± 35 |
| BMS-906024-PLGA | 177 ± 16 |

Figure 8:
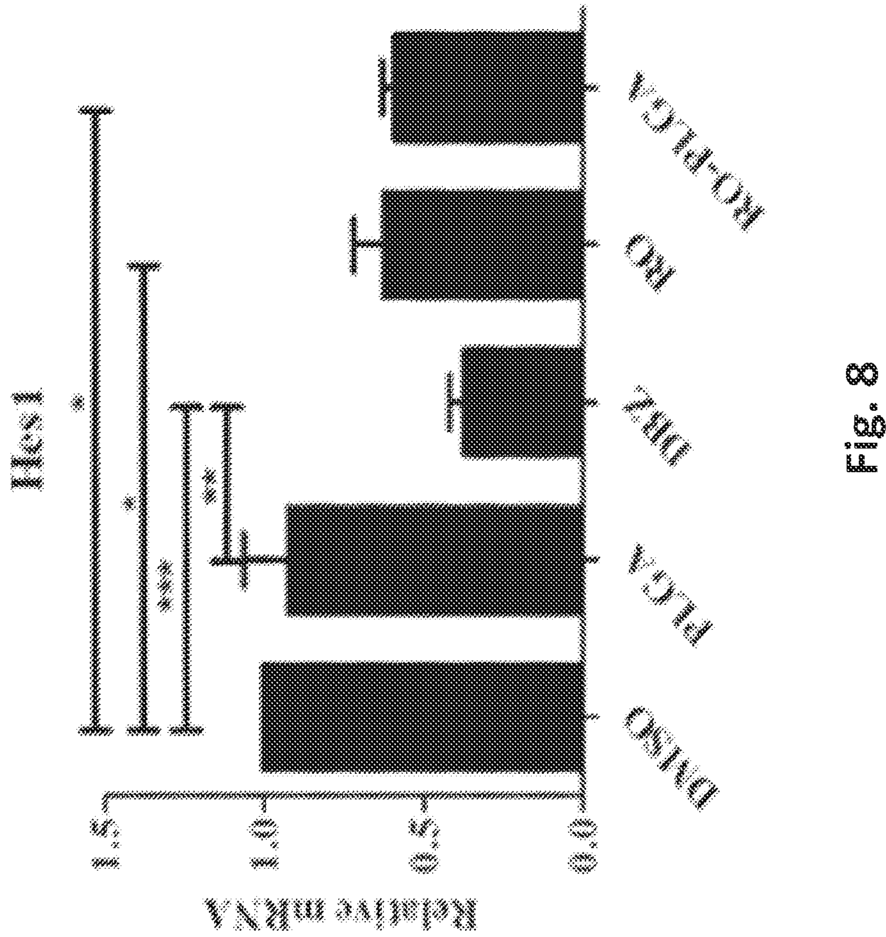
FIG. 8 is a graph showing the effect of RO4929097-PLGA NPs on the Notch signaling target gene.

Effect of RO4929097-PLGA NPs on the Notch signaling target gene. 3T3-L1 preadipocytes were treated with DMSO, PLGA NPs (0.1 mg/mL), DBZ (10 μM), RO4929097 (1 μM) or RO4929097-PLGA NPs (0.1 mg/ml) for 12 h at 37° C. in a 5% CO2 incubator. The Notch target Hes1 mRNA expression was analyzed by qRT-PCR (FIG. 8). Each bar is the mean±SEM of 4 to 5 replicates in each group and the data were analyzed by one-way ANOVA followed by Tukey's post hoc comparison test. Asterisks refer to statistical difference between the indicated treatment groups (*$p<0.05$, $p<0.01$, and *$p<0.001$). The RO4929097-PLGA NPs down-regulated the Notch signaling target gene encoding Hes-1, which is involved in the process of adipocyte browning.

Figures 9A, 9B, 9C, 9D, 9E, 9F, 9G, 9H:
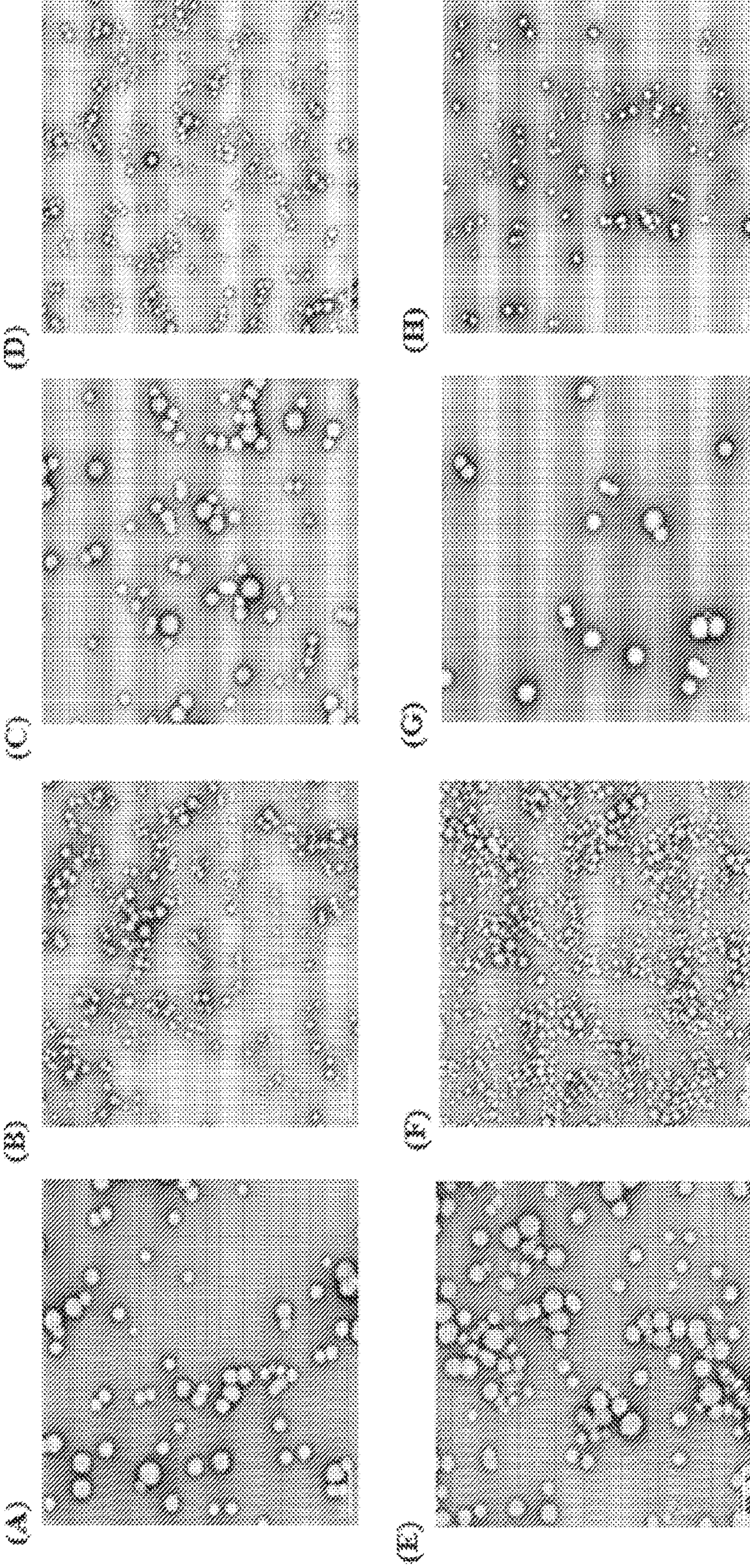
FIGS. 9A-9H is a series of TEM images showing morphological images of various γ-secretase inhibitor-loaded PLGA NPs. The TEM image of RO4929097-PLGA NPs at 500 nm (FIG. 9A) and 200 nm (FIG. 9B); PF-03084014-PLGA NPs at 500 nm (FIG. 9C) and 200 nm (FIG. 9C); LY3039478-PLGA NPs at 500 nm (FIG. 9E) and 200 nm (FIG. 9F); and BMS-906024-PLGA NPs at 500 nm (FIG. 9G) and 200 nm (FIG. 9H).

Morphology of PLGA nanoparticles. The morphologies of various γ-secretase inhibitor-loaded PLGA NPs was determined by TEM. The 0.1 mg of nanoparticulate along with the equal concentration of sucrose cryoprotectant added suspension was diluted in 1 ml distilled water and the transmission electron microscope (TEM) images were taken using FEI Tecnai G2 20 TEM at 200 kV. The TEM images are shown in FIGS. 9A-9H: RO4929097-PLGA NPs at 500 nm (FIG. 9A) and 200 nm (FIG. 9B); PF-03084014-PLGA NPs at 500 nm (FIG. 9C) and 200 nm (FIG. 9C); LY3039478-PLGA NPs at 500 nm (FIG. 9E) and 200 nm (FIG. 9F); and BMS-906024-PLGA NPs at 500 nm (FIG. 9G) and 200 nm (FIG. 9H).

Example 3: Usable Cryoprotectant in the PLGA Nanoparticle Formulation Lyophilization Process Freeze-drying or lyophilization is the common practice to store and improve the long-term stability of colloidal nanoparticles. However, the freeze-drying process may result in the alterations of nanoparticle physical properties, as well as affecting the particle size, release characteristics, and robustness, with subsequent effects on the encapsulated payload release and stability.

Hence, different excipients like trehalose, sucrose, fructose, glucose, lactose, mannitol, ribose, maltose, mannose, dextrose, sorbitol, glycine, dextran, gelatine, poly(vinyl pyrrolidone), poly(vinyl alcohol), and aerosil, as cryoprotectant agent will be used to increase the PLGA nanoparticles formulation physical stability during freeze-drying, to prevent their aggregation and protect them against the mechanical stress of ice crystals. These cryoprotectants are important, because they affect the glass transition temperature, which is important to obtain a freeze-dried cake with a stable amorphous form, a high redispersion speed, appropriate residual moisture content, and a good cargo protection and stabilization upon storage.

Abbreviations

BAT: Brown adipose tissues; C/EBPs: CCAAT/enhancer binding protein family proteins; CIDEA: Cell death-inducing DNA fragmentation factor alpha-like effector A; COX5B: Cytochrome c oxidase subunit 5B; DAPT: (N—[N-(3,5-Difluorophenacetyl)-1-alanyl]-S-phenylglycine t-butyl ester); DI02: Type 2 deiodinase; FABP4: Fatty acid binding protein 4; GSIs: γ-secretase inhibitors; NICD: Notch intracellular domain; PPARs: Peroxisomal proliferator-activated receptor family proteins; PPARGC1α; Peroxisome proliferator-activated receptor gamma coactivator 1-alpha; PRDM16: PR domain containing 16; RBPJ: Recombination signal binding protein for immunoglobulin kappa J region; TMEM26: Transmembrane protein 26; UCP1: Uncoupling protein 1; WAT: White adipose tissue; T2DM: Type 2 Diabetes Mellitus.

EQUIVALENTS

The details of one or more embodiments of the disclosure are set forth in the accompanying description above. Although any methods and materials similar or equivalent to those described herein can be used in the practice or testing of the present disclosure, the preferred methods and materials are now described. Other features, objects, and advantages of the disclosure will be apparent from the description and from the claims.

In the specification and the appended claims, the singular forms include plural referents unless the context clearly dictates otherwise. Unless defined otherwise, all technical and scientific terms used herein have the same meaning as commonly understood by one of ordinary skill in the art to which this disclosure belongs. All patents and publications cited in this specification are incorporated by reference.

The foregoing description has been presented only for the purposes of illustration and is not intended to limit the disclosure to the precise form disclosed, but by the claims appended hereto.

Those skilled in the art will recognize that numerous modifications can be made to the specific implementations described above. The implementations should not be limited to the particular limitations described. Other implementations may be possible.

While the disclosure been illustrated and described in detail in the drawings and foregoing description, the same is to be considered as illustrative and not restrictive in character, it being understood that only certain embodiments have been shown and described and that all changes and modifications that come within the spirit of the invention are desired to be protected. It is intended that the scope of the present methods and apparatuses be defined by the following claims. However, it must be understood that this disclosure may be practiced otherwise than is specifically explained and illustrated without departing from its spirit or scope. It should be understood by those skilled in the art that various alternatives to the embodiments described herein may be employed in practicing the claims without departing from the spirit and scope as defined in the following claims.

REFERENCES CITED (INCORPORATED HEREIN BY REFERENCE)

1. Smith K B, Smith M S. Obesity Statistics. Prim Care—Clin Off Pract. Elsevier; 2016; 43:121-35.
2. Rosen E D, Spiegelman B M. Adipocytes as regulators of energy balance and glucose homeostasis. Nature. Nature Publishing Group; 2006; 444:847-53.
3. Lshibashi J, Seale P. Beige can be slimming Science (80-). American Association for the Advancement of Science; 2010; 328:1113-4.
4. Wu J, Bostrom P, Sparks L M, Ye L, Choi J H, Giang A H, et al. Beige adipocytes are a distinct type of thermogenic fat cell in mouse and human Cell. Elsevier; 2012; 150:366-76.
5. Artavanis-Tsakonas S, Rand M D, Lake R J. Notch signaling: cell fate control and signal integration in development. Science (80-). American Association for the Advancement of Science; 1999; 284:770-6.
6. Luo D, Renault V M, Rando T A. The regulation of Notch signaling in muscle stem cell activation and postnatal myogenesis. Semin Cell Dev Biol. Elsevier; 2005; 16:612-22.
7. Urs S, Turner B, Tang Y, Rostama B, Small D, Liaw L. Effect of soluble Jagged1-mediated inhibition of Notch signaling on proliferation and differentiation of an adipocyte progenitor cell model. Adipocyte. Taylor & Francis; 2012; 1:46-57.
8. Kadesch T. Notch signaling: The demise of elegant simplicity. Curr Opin Genet Dev. Elsevier; 2004; 14:506-12.
9. Schroeter E H, Kisslinger J A, Kopan R. Notch-1 signalling requires ligand-induced proteolytic release of intracellular domain. Nature. Nature Publishing Group; 1998; 393:382-6.
10. Gregoire F M, Smas C M, Sul H S. Understanding adipocyte differentiation. Physiol Rev. American Physiological Society Bethesda, MD; 1998; 78:783-809.
11. Lai P Y, Tsai C Bin, Tseng M J. Active form Notch4 promotes the proliferation and differentiation of 3T3-L1 preadipocytes. Biochem Biophys Res Commun. Elsevier; 2013; 430:1132-9.
12. Osathanon T, Subbalekha K, Sastravaha P, Pavasant P. Notch signalling inhibits the adipogenic differentiation of single-cell-derived mesenchymal stem cell clones isolated from human adipose tissue. Cell Biol Int. Wiley Online Library; 2012; 36:1161-70.
13. Woo H N, Park J S, Gwon A R, Arumugam T V., Jo D G Alzheimer's disease and Notch signaling. Biochem Biophys Res Commun. Elsevier; 2009; 390:1093-7.
14. SpringWorks Therapeutics. No Title [Internet]. 2020. Available from: clinicaltrials.gov/ct2/show/NCT03785964
15. Bi P, Shan T, Liu W, Yue F, Yang X, Liang X R, et al. Inhibition of Notch signaling promotes browning of white adipose tissue and ameliorates obesity. Nat Med. 2014; 20:911-8.
16. Jiang C, Cano-Vega M A, Yue F, Kuang L, Narayanan N, Uzunalli G, et al. Dibenzazepine-Loaded Nanoparticles Induce Local Browning of White Adipose Tissue to Counteract Obesity. Mol Ther [Internet]. Elsevier Ltd.;

2017; 25:1718-29. Available from: http://dx.doi.org/10.1016/j.ymthe.2017.05.020

17. Wei P, Walls M, Qiu M, Ding R, Denlinger R H, Wong A, et al. Evaluation of selective γ-secretase inhibitor PF-03084014 for its antitumor efficacy and gastrointestinal safety to guide optimal clinical trial design. Mol Cancer Ther. AACR; 2010; 9:1618-28.
18. Kelly A, Houston S A, Sherwood E, Casulli J, Travis M A. Regulation of Innate and Adaptive Immunity by TGFβ. Adv Immunol. Nature Publishing Group; 2017; 134:137-233.
19. Gridley T. Notch signaling in the vasculature. Curr Top Dev Biol. Elsevier; 2010. p. 277-309.
20. Mourikis P, Sambasivan R, Castel D, Rocheteau P, Bizzarro V, Tajbakhsh S. A critical requirement for notch signaling in maintenance of the quiescent skeletal muscle stem cell state. Stem Cells. Wiley Online Library; 2012; 30:243-52.
21. Garcés C, Ruiz-Hidalgo M J, De Mora J F, Park C, Miele L, Goldstein J, et al. Notch-1 controls the expression of fatty acid-activated transcription factors and is required for adipogenesis. J Biol Chem. ASBMB; 1997; 272: 29729-34.
22. Song B Q, Chi Y, Li X, Du W J, Han Z B, Tian J J, et al. Inhibition of Notch Signaling Promotes the Adipogenic Differentiation of Mesenchymal Stem Cells Through Autophagy Activation and PTEN-PI3K/AKT/mTOR Pathway. Cell Physiol Biochem. Karger Publishers; 2015; 36:1991-2002.
23. Lonetti A, Cappellini A, Sparta A M, Chiarini F, Buontempo F, Evangelisti C, et al. PI3K pan-inhibition impairs more efficiently proliferation and survival of T-cell acute lymphoblastic leukemia cell lines when compared to isoform-selective PI3K inhibitors. Oncotarget. Impact Journals, LLC; 2015; 6:10399.
24. Luistro L, He W, Smith M, Packman K, Vilenchik M, Carvajal D, et al. Preclinical profile of a potent γ-secretase inhibitor targeting notch signaling with in vivo efficacy and pharmacodynamic properties. Cancer Res. AACR; 2009; 69:7672-80.
25. Lee H W, Kim S J, Choi I J, Song J, Chun K H. Targeting Notch signaling by γ-secretase inhibitor I enhances the cytotoxic effect of 5-FU in gastric cancer. Clin Exp Metastasis. Springer; 2015; 32:593-603.
26. Han J, Ma I, Hendzel M J, Allalunis-Turner J. The cytotoxicity of γ-secretase inhibitor I to breast cancer cells is mediated by proteasome inhibition, not by γ-secretase inhibition. Breast Cancer Res. Springer; 2009; 11:R57.
27. Huang D, Narayanan N, Cano-Vega M A, Jia Z, Ajuwon K M, Kuang S, et al. Nanoparticle-Mediated Inhibition of Notch Signaling Promotes Mitochondrial Biogenesis and Reduces Subcutaneous Adipose Tissue Expansion in Pigs. iScience. Elsevier; 2020; 23:101167.
28. Ross D A, Rao P K, Kadesch T. Dual Roles for the Notch Target Gene Hes-1 in the Differentiation of 3T3-L1 Preadipocytes. Mol Cell Biol. Am Soc Microbiol; 2004; 24:3505-13.
29. Ross D A, Hannenhalli S, Tobias J W, Cooch N, Shiekhattar R, Kadesch T. Functional analysis of Hes-1 in preadipocytes. Mol Endocrinol. Oxford University Press; 2006; 20:698-705.
30. Kajimura S, Seale P, Spiegelman B M. Transcriptional control of brown fat development. Cell Metab. Elsevier; 2010; 11:257-62.
31. Shapira S N, Seale P. Transcriptional Control of Brown and Beige Fat Development and Function. Obesity. Elsevier; 2019; 27:13-21.
32. Nedergaard J, Golozoubova V, Matthias A, Asadi A, Jacobsson A, Cannon B. UCP1: The only protein able to mediate adaptive non-shivering thermogenesis and metabolic inefficiency. Biochim Biophys Acta—Bioenerg. Elsevier; 2001; 1504:82-106.
33. Shabalina I G, Petrovic N, deJong JMA, Kalinovich A V., Cannon B, Nedergaard J. UCP1 in Brite/Beige adipose tissue mitochondria is functionally thermogenic. Cell Rep. Elsevier; 2013; 5:1196-203.
34. Huang Y, Yang X, Wu Y, Jing W, Cai X, Tang W, et al. γ-secretase inhibitor induces adipogenesis of adipose-derived stem cells by regulation of Notch and PPAR-γ. Cell Prolif. Wiley Online Library; 2010; 43:147-56.

What is claimed is:

1. A γ-secretase inhibitor (GSI), or a derivative, prodrug, or pharmaceutically acceptable salt thereof, which increases expression of uncoupling protein-1 (UCP-1), having the structure shown below:

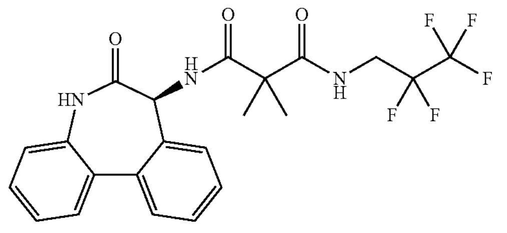 [SMILES: CC(C)(C(=O)NCC(F)(F)C(F)(F)F)C(=O)N[C@@H]1C(=O)Nc2ccccc2-c2ccccc21]

including pharmaceutically suitable acid addition salts, optically pure enantiomers, racemates, and diastereomeric mixtures thereof.

2. A pharmaceutical composition comprising the γ-secretase inhibitor (GSI) of claim 1, or a derivative, a prodrug, or a pharmaceutically acceptable salt thereof, including acid addition salts, optically pure enantiomers, racemates, and diastereomeric mixtures thereof.

3. A method of increasing browning of white adipose tissue in a subject in need thereof, which method comprises administering to the subject a Notch signaling inhibitor compound of claim 1 that increases expression of uncoupling protein-1 (UCP-1).

4. The method of claim 3, wherein the subject has, or is at risk for developing, obesity.

5. The method of claim 3, wherein the subject has a body mass index (BMI) of about or at least about 25, 30, 35, or 40 kg/m$^2$.

6. The method of claim 3, wherein the subject has class 1 obesity (BMI of about 30-35 kg/m$^2$), class II obesity (BMI of about 35-40 kg/m$^2$), or class III obesity (BMI greater than about 40 kg/m$^2$).

7. The method of claim 3, wherein the subject has fasting glucose levels of about or at least about 100 mg/dL.

8. The method of claim 7, wherein the subject has fasting glucose levels of about 100-125 mg/dL (prediabetes) or about 126 mg/dL or higher (diabetes).

9. The method of claim 3, wherein the Notch signaling inhibitor compound is a γ-secretase inhibitor (GSI), or a derivative, prodrug, or pharmaceutically acceptable salt thereof.

10. The method of claim 3, wherein the Notch signaling inhibitor compound is administered to the subject at a site, or proximal to a site, which contains the white adipose tissue.

11. The method of claim 3, which increases expression of UCP-1 by about or at least about 2, 5, 10, 50, 100, 500, or 1000-fold relative to a baseline reference or control.

12. The method of claim 3, which increases browning of white adipose tissue in the subject by about or at least about 5, 10, 20, 30, 40, 50, 60, 70, 80, 90, or 100%, relative to a baseline reference or control.

13. The method of claim 3, which reduces white adipose tissue in the subject, optionally by about or at least about 5, 10, 20, 30, 40, or 50% or more, relative to a baseline reference or control.

14. The method of claim 3, which reduces body weight in the subject by about or at least about 5, 10, 20, 30, 40, or 50% or more, relative to a baseline reference or control, or by about or at least about 5, 10, 20, 30, 40, 50, 60, 70, 80, 90, or 100 kg or more.

15. The method of claim 3, which reduces body mass index (BMI) in the subject by about or at least about 1, 2, 3, 4, 5, 6, 7, 8, 9, 10, 11, 12, 13, 14, 15, 16, 17, 18, 19, or 20 kg/m$^2$.

16. The method of claim 3, which improves glucose homeostasis in the subject.

17. The method of claim 3, which reduces levels of fasting glucose in the subject by about or at least about 10, 20, 30, 40, or 50% or more, relative to a baseline reference or control, or to a level of about or less than about 100 mg/dL.

18. The method of claim 3, which increases glucose tolerance in the subject by about or at least about 10, 20, 30, 40, or 50% or more, relative to a baseline reference or control, or to a level of about or less than about 140 mg/dL, as measured in an oral glucose tolerance test.

* * * * *

SEQUENCE LISTING

```
<160> NUMBER OF SEQ ID NOS: 18

<210> SEQ ID NO 1
<211> LENGTH: 21
<212> TYPE: DNA
<213> ORGANISM: Artificial sequence
<220> FEATURE:
<223> OTHER INFORMATION: Primer Hes1

<400> SEQUENCE: 1

gcacagaaag tcatcaaagc c                                              21


<210> SEQ ID NO 2
<211> LENGTH: 21
<212> TYPE: DNA
<213> ORGANISM: Artificial sequence
<220> FEATURE:
<223> OTHER INFORMATION: Primer Hes1 reverse

<400> SEQUENCE: 2

ttgatctggg tcatgcagtt g                                              21


<210> SEQ ID NO 3
```

-continued

<211> LENGTH: 19
<212> TYPE: DNA
<213> ORGANISM: Artificial sequence
<220> FEATURE:
<223> OTHER INFORMATION: Primer Fabp4

<400> SEQUENCE: 3
gatgcctttg tgggaacct 19

<210> SEQ ID NO 4
<211> LENGTH: 19
<212> TYPE: DNA
<213> ORGANISM: Artificial sequence
<220> FEATURE:
<223> OTHER INFORMATION: Primer Fabp4 reverse

<400> SEQUENCE: 4
ctgtcgtctg cggtgattt 19

<210> SEQ ID NO 5
<211> LENGTH: 22
<212> TYPE: DNA
<213> ORGANISM: Artificial sequence
<220> FEATURE:
<223> OTHER INFORMATION: Primer Ppargc1l alpha

<400> SEQUENCE: 5
agccgtgacc actgacaacg ag 22

<210> SEQ ID NO 6
<211> LENGTH: 23
<212> TYPE: DNA
<213> ORGANISM: Artificial sequence
<220> FEATURE:
<223> OTHER INFORMATION: Primer Ppargc1 alpha reverse

<400> SEQUENCE: 6
gctgcatggt tctgagtgct aag 23

<210> SEQ ID NO 7
<211> LENGTH: 21
<212> TYPE: DNA
<213> ORGANISM: Artificial sequence
<220> FEATURE:
<223> OTHER INFORMATION: Primer Cox5B

<400> SEQUENCE: 7
ttcaaggtta cttcgcggag t 21

<210> SEQ ID NO 8
<211> LENGTH: 22
<212> TYPE: DNA
<213> ORGANISM: Artificial sequence
<220> FEATURE:
<223> OTHER INFORMATION: Primer Cox5B reverse

<400> SEQUENCE: 8
cgggactaga ttagggtctt cc 22

<210> SEQ ID NO 9
<211> LENGTH: 21
<212> TYPE: DNA
<213> ORGANISM: Artificial sequence
<220> FEATURE:
<223> OTHER INFORMATION: Primer Tmem26

<400> SEQUENCE: 9

-continued gaaaccagta ttgcagcacc c 21

<210> SEQ ID NO 10
<211> LENGTH: 20
<212> TYPE: DNA
<213> ORGANISM: Artificial sequence
<220> FEATURE:
<223> OTHER INFORMATION: Primer Tmem26 reverse

<400> SEQUENCE: 10
ccagaccggt tcacatacca 20

<210> SEQ ID NO 11
<211> LENGTH: 21
<212> TYPE: DNA
<213> ORGANISM: Artificial sequence
<220> FEATURE:
<223> OTHER INFORMATION: Primer Ucp1

<400> SEQUENCE: 11
aggcttccag taccattagg t 21

<210> SEQ ID NO 12
<211> LENGTH: 22
<212> TYPE: DNA
<213> ORGANISM: Artificial sequence
<220> FEATURE:
<223> OTHER INFORMATION: Primer Ucp1 reverse

<400> SEQUENCE: 12
ctgagtgagg caaagctgat tt 22

<210> SEQ ID NO 13
<211> LENGTH: 22
<212> TYPE: DNA
<213> ORGANISM: Artificial sequence
<220> FEATURE:
<223> OTHER INFORMATION: Primer Cidea

<400> SEQUENCE: 13
tgacattcat gggattgcag ac 22

<210> SEQ ID NO 14
<211> LENGTH: 22
<212> TYPE: DNA
<213> ORGANISM: Artificial sequence
<220> FEATURE:
<223> OTHER INFORMATION: Primer Cidea reverse

<400> SEQUENCE: 14
ggccagttgt gatgactaag ac 22

<210> SEQ ID NO 15
<211> LENGTH: 19
<212> TYPE: DNA
<213> ORGANISM: Artificial sequence
<220> FEATURE:
<223> OTHER INFORMATION: Primer Prdm16

<400> SEQUENCE: 15
cagcacggtg aagccattc 19

<210> SEQ ID NO 16
<211> LENGTH: 17
<212> TYPE: DNA

-continued

```
<213> ORGANISM: Artificial sequence
<220> FEATURE:
<223> OTHER INFORMATION: Primer Prdm16 reverse

<400> SEQUENCE: 16

gcgtgcatcc gcttgtg                                              17


<210> SEQ ID NO 17
<211> LENGTH: 22
<212> TYPE: DNA
<213> ORGANISM: Artificial sequence
<220> FEATURE:
<223> OTHER INFORMATION: Primer Dio2

<400> SEQUENCE: 17

aattatgcct cggagaagac cg                                        22


<210> SEQ ID NO 18
<211> LENGTH: 21
<212> TYPE: DNA
<213> ORGANISM: Artificial sequence
<220> FEATURE:
<223> OTHER INFORMATION: Primer Dio2 reverse

<400> SEQUENCE: 18

ggcagttgcc tagtgaaagg t                                         21
```